United States Patent
Hillman et al.

(10) Patent No.: US 9,655,523 B2
(45) Date of Patent: May 23, 2017

(54) OPTICAL IMAGING OR SPECTROSCOPY SYSTEMS AND METHODS

(75) Inventors: Elizabeth Marjorie Clare Hillman, New York, NY (US); Sean A. Burgess, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1215 days.

(21) Appl. No.: 12/655,325

(22) Filed: Dec. 29, 2009

(65) Prior Publication Data

US 2010/0168586 A1 Jul. 1, 2010

Related U.S. Application Data

(63) Continuation of application No. PCT/US2008/008081, filed on Jun. 27, 2008.
(Continued)

(51) Int. Cl.
*A61B 5/05* (2006.01)
*A61B 5/00* (2006.01)
(Continued)

(52) U.S. Cl.
CPC .......... *A61B 5/0064* (2013.01); *A61B 5/0066* (2013.01); *A61B 5/0071* (2013.01);
(Continued)

(58) Field of Classification Search
CPC ... A61B 5/0064; A61B 5/0066; A61B 5/0071; A61B 5/0073; A61B 5/0075
See application file for complete search history.

(56) References Cited

U.S. PATENT DOCUMENTS 4,965,441 A 10/1990 Picard
5,006,721 A 4/1991 Cameron et al.
(Continued)

FOREIGN PATENT DOCUMENTS

WO WO-2009/005748 A1 1/2009

OTHER PUBLICATIONS

Hillman et al, Laminar optical tomography: high-resolution 3D functional imaging of superficial tissues, Proc. of SPIE vol. 6143 61431M-1, 2006.*
(Continued)

*Primary Examiner* — Joel Lamprecht
(74) *Attorney, Agent, or Firm* — Potomac Law Group, PLLC; Mark Catan

(57) ABSTRACT

Optical imaging or spectroscopy described can use laminar optical tomography (LOT), diffuse correlation spectroscopy (DCS), or the like. An incident beam is scanned across a target. An orthogonal or oblique optical response can be obtained, such as concurrently at different distances from the incident beam. The optical response from multiple incident wavelengths can be concurrently obtained by dispersing the response wavelengths in a direction orthogonal to the response distances from the incident beam. Temporal correlation can be measured, from which flow and other parameters can be computed. An optical conduit can enable endoscopic or laparoscopic imaging or spectroscopy of internal target locations. An articulating arm can communicate the light for performing the LOT, DCS, or the like. The imaging can find use for skin cancer diagnosis, such as distinguishing lentigo maligna (LM) from lentigo maligna melanoma (LMM).

24 Claims, 16 Drawing Sheets
(3 of 16 Drawing Sheet(s) Filed in Color)

Related U.S. Application Data

(60) Provisional application No. 60/937,724, filed on Jun. 29, 2007, provisional application No. 61/000,792, filed on Oct. 29, 2007, provisional application No. 61/130,904, filed on Jun. 4, 2008.

(51) Int. Cl.
| | |
|---|---|
| *G01J 3/28* | (2006.01) |
| *G01J 3/42* | (2006.01) |
| *G01J 3/457* | (2006.01) |
| *G02B 23/24* | (2006.01) |
| *G02B 26/10* | (2006.01) |

(52) U.S. Cl.
CPC .......... *A61B 5/0073* (2013.01); *A61B 5/0075* (2013.01); *A61B 5/444* (2013.01); *A61B 5/445* (2013.01); *G01J 3/2889* (2013.01); *G01J 3/42* (2013.01); *G01J 3/457* (2013.01); *G02B 23/2476* (2013.01); *G02B 26/101* (2013.01); *A61B 5/0088* (2013.01); *A61B 2562/0238* (2013.01); *A61B 2562/0242* (2013.01)

(56) References Cited

U.S. PATENT DOCUMENTS

| | | | |
|---|---|---|---|
| 5,305,092 | A | 4/1994 | Mimura et al. |
| 5,412,473 | A * | 5/1995 | Rosencwaig et al. ........ 356/451 |
| 5,453,851 | A | 9/1995 | Faulhaber |
| 5,489,985 | A | 2/1996 | Mochida et al. |
| 5,493,388 | A | 2/1996 | Adachi |
| 5,510,889 | A | 4/1996 | Herr |
| 5,627,308 | A | 5/1997 | Dahneke |
| 5,719,399 | A | 2/1998 | Alfano et al. |
| 5,790,243 | A | 8/1998 | Herr |
| 5,914,495 | A | 6/1999 | Ishizuka et al. |
| 6,115,114 | A | 9/2000 | Berg et al. |
| 6,208,749 | B1 | 3/2001 | Gutkowicz-Krusin et al. |
| 6,341,036 | B1 | 1/2002 | Tearney et al. |
| 6,399,936 | B1 | 6/2002 | Hang et al. |
| 6,480,287 | B2 | 11/2002 | Lee et al. |
| 6,615,063 | B1 | 9/2003 | Ntziachristos et al. |
| 6,674,893 | B1 | 1/2004 | Abe et al. |
| 6,775,404 | B1 | 8/2004 | Pagoulatos et al. |
| 6,809,815 | B2 | 10/2004 | Knebel |
| 6,825,930 | B2 | 11/2004 | Cronin et al. |
| 7,107,116 | B2 | 9/2006 | Geng |
| 7,147,153 | B2 | 12/2006 | Rowe et al. |
| 7,231,243 | B2 | 6/2007 | Tearney et al. |
| 8,254,020 | B2 | 8/2012 | Holy et al. |
| 8,290,358 | B1 | 10/2012 | Georgiev |
| 8,619,237 | B2 | 12/2013 | Hillman et al. |
| 2002/0049389 | A1* | 4/2002 | Abreu ........................ 600/558 |
| 2003/0142934 | A1 | 7/2003 | Pan et al. |
| 2004/0054248 | A1 | 3/2004 | Kimchy et al. |
| 2004/0054270 | A1 | 3/2004 | Pewzner et al. |
| 2005/0171439 | A1 | 8/2005 | Maschke et al. |
| 2006/0092315 | A1* | 5/2006 | Payonk et al. ................ 348/370 |
| 2007/0035721 | A1 | 2/2007 | Toshikiyo et al. |
| 2008/0225299 | A1 | 9/2008 | Ono |
| 2009/0296207 | A1 | 12/2009 | Goelles et al. |
| 2012/0140240 | A1 | 6/2012 | Hillman et al. |

OTHER PUBLICATIONS

"Applications in Confocal Microscopy: Fluorescence Lifetime Imaging Microscopy (FLIM),", © 2004-2009 Olympus Corporation, [online]. [retrieved Dec. 9, 2010}. Retrieved from the Internet: <URL: http://www.olympusfluoview.com/applications/flimintro.html>, 3 pgs.

Dunsby, C. "Optically sectioned imaging by oblique plane microscopy", *Optics Express*, 16(25), (2008), 20306-20316.

Dwyer, P. J., et al., "Confocal Reflectance Theta Line Scanning Microscope for Imaging Human Skin In Vivo", *Optics Letters*, 31(7), 942-944.

Dwyer, P. J., et al., "Confocal theta line-scanning microscope for imaging human tissues", *Applied Optics*, 46(10), (2007), 1843-1851.

Dyba, M., et al., "STED-Microscopy . . . Overcomes the diffraction limit in a fundamental way", [online]. [retrieved Dec. 9, 2010]. Retrieved from the Internet: <URL: http://www.mpibpc.mpg.de/groups/hell/STED.htm>, 3 pgs.

Fahrbach, F. 0., et al., "Microscopy With Self-Reconstructing Beams", *Nature Photonics*, 4, (2010), 780-785.

Huisken, J., et al., "Selective plane illumination microscopy techniques in developmental biology", *Development*, 136, (2009), 1963-1975.

"DermLite Pro DP-R: The Ultimate in Handheld Dermoscopy", http://www.dermlite.com/pro.html, (2008).

"International Application Serial No. PCT/US2008/008081, International Search Report and Written Opinion mailed Oct. 1, 2008", P220, 12 pgs.

"Mohs Surgery with the VivaCell 2500", http://www.lucid-tech.com/medical-imagers/vivacell.asp, (Downloaded Aug. 29, 2008).

"Skin measurement, In vivo, In seconds", http://www.astronclinica.com/products/siametrics.htm, Copyright Astron Clinica 2007, (2007).

"The MelaFind System", http://www.eo-sciences.com/technology1.html, (Downloaded Aug. 29, 2008).

Barton, Jennifer Kehlet, "Optical coherence tomography", in AccessScience@McGraw-Hill, http://www.accessscience.com, DOI 10.1036/1097-8542.757714, Copyright 2007, (Downloaded Aug. 29, 2008).

Corlu, A., et al., "Diffuse optical tomography with spectral constraints and wavelength optimization", *Applied Optics*, 44(11), (Apr. 10, 2005), 2082-2093.

Corlu, A., et al., "Uniqueness and wavelength optimization in continuous-wave multispectral diffuse optical tomography", *Optics Letters*, 28(23), (Dec. 1, 2003), 2339-2341.

Hillman, E. M., et al., "Depth-resolved optical imaging and microscopy of vascular compartment dynamics during somatosensory stimulation.", *Neuroimage*, 35(1), (Mar. 2007), 89-104.

Hillman, E. M., et al., "Supplemental Material for: Depth-resolved Optical Imaging and Microscopy of Vascular Compartment Dynamics During Somatosensory Stimulation", http://www.nmr.mgh.harvard.edu/PMI/PDF/2007/Hillman_NI_2007_supp.pdf, Neuroimage. Mar. 2007;35(1):89-104, (2007), 1-11.

Hillman, Elizabeth, "Experimental and theoretical investigations of near infrared tomographic imaging methods and clinical applications.", *Thesis submitted for the degree of Doctor of Philosophy (Ph.D.) at the University of London*, (Feb. 2002), 1-356.

Li, Ang, et al., "Optimal linear inverse solution with multiple priors in diffuse optical tomography", *Applied Optics*, 44(10), (Apr. 1, 2005), 1948-1956.

Stoecker, William, "Automatic Detection of Critical Dermoscopy Features for Melanoma Diagnosis—Grant No. 2R44CA101639-02A2", http://crisp.cit.nih.gov/crisp/CRISP_LIB.getdoc?textkey=7163231&p_grant_num=2R44CA101639-02A2&p_query=(melanoma+%26+detection)&ticket=67102869&p_audit_session_id=334829146&p_audit_score=39&p_audit_numfound=3&p_keywords=melanoma+detection, CRISP (Computer Retrieval of Information on Scientific Projects) Database, (2006).

Timmins, Graham, "Molecular imaging of melanoma by EPR", *CRISP (Computer Retrieval of Information on Scientific Projects) Database*, http://crisp.cit.nih.gov/crisp/CRISP_LIB.getdoc?textkey=7048244&p_grant_num=1R21CA113687-01A1&p_query=(melanoma+%26+detection)&ticket=67102869&p_audit_session_id=334829146&p_audit_score=8&p_audit_numfound=134&p_keywords=melanoma+detection, (2006).

"U.S. Appl. No. 12/961,074, Non Final Office Action mailed Mar. 28, 2013", 12 pgs.

"U.S. Appl. No. 12/961,074, Response filed Mar. 19, 2013 to Restriction Requirement mailed Oct. 19, 2012", 10 pgs.

(56) References Cited

OTHER PUBLICATIONS

"U.S. Appl. No. 12/961,074, Restriction Requirement mailed Oct. 19, 2012", 8 pgs.
U.S. Appl. No. 12/961,074, Response filed Jul. 29, 2013 to Non Final Office Action mailed Mar. 28, 2013, 16 pgs.
U.S. Appl. No. 12/961,074, Examiner Interview Summary mailed Aug. 6, 2013, 3 pgs.
U.S. Appl. No. 12/961,074, Notice of Allowance mailed Aug. 21, 2013, 8 pgs.
Hillman, E.M.C., et al., "Laminar Optical Tomography: demonstration of millimeterscale depth-resolved imaging in turbid media", Opt. Lett., Jul. 15, 2004, vol. 29(14), p. 1650-2.
Holekamp et al., "Fast Three-Dimensional Fluorescence Imaging of Activity in Neural Populations by Objective-Coupled Planar Illumination Microscopy", Neuron, Mar. 13, 2008, vol. 57, pp. 661-672.
Swoger et al., "Light-Sheet-Based Fluorescence Microscopy for Three-Dimensional Imaging of Biological Samples", Adapted from Imaging: A Laboratory Manual (ed. Yuste). CSHL Press, Cold Spring Harbor, NY, USA, Jan. 1, 2011, copyrighted 2014 (downloaded Jun. 5, 2016).
Truscott et al., "Determining 3D Flow Fields via Multi-camera Light Field Imaging", Journal of Visualized Experiments: Jove, Mar. 6, 2013, vol. 73, p. 4325.

\* cited by examiner

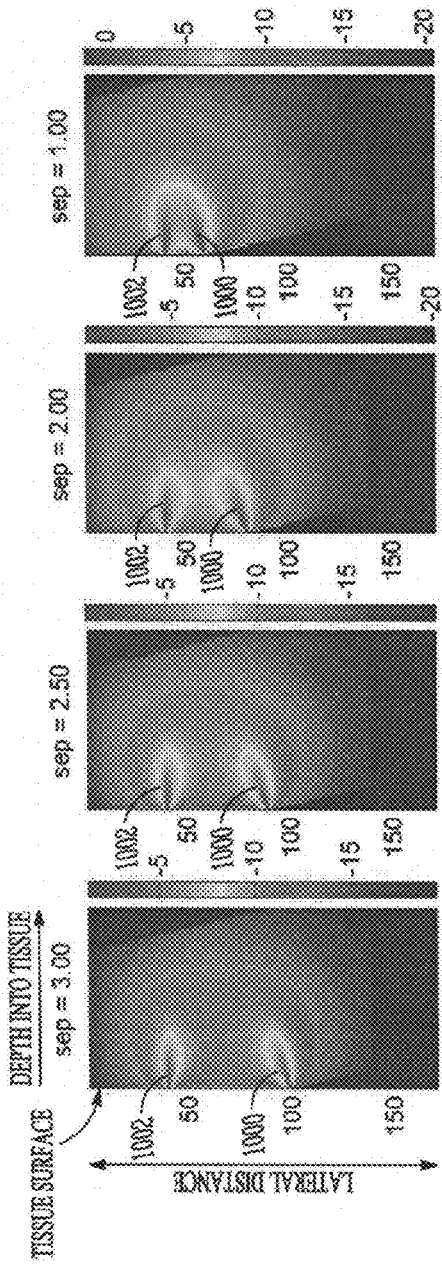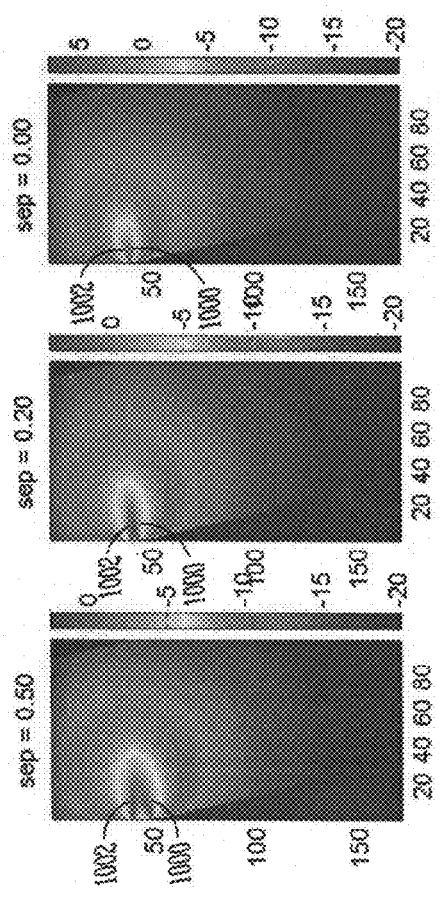

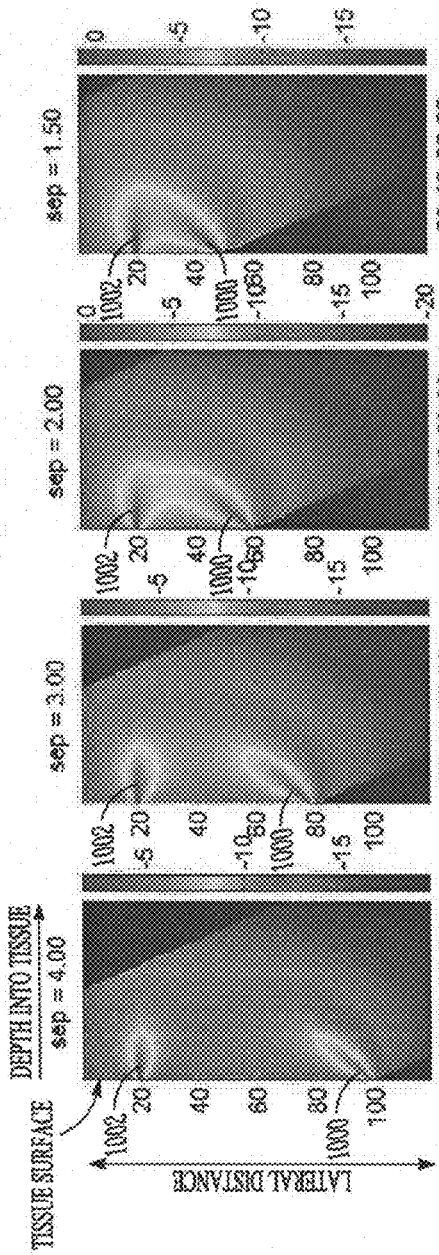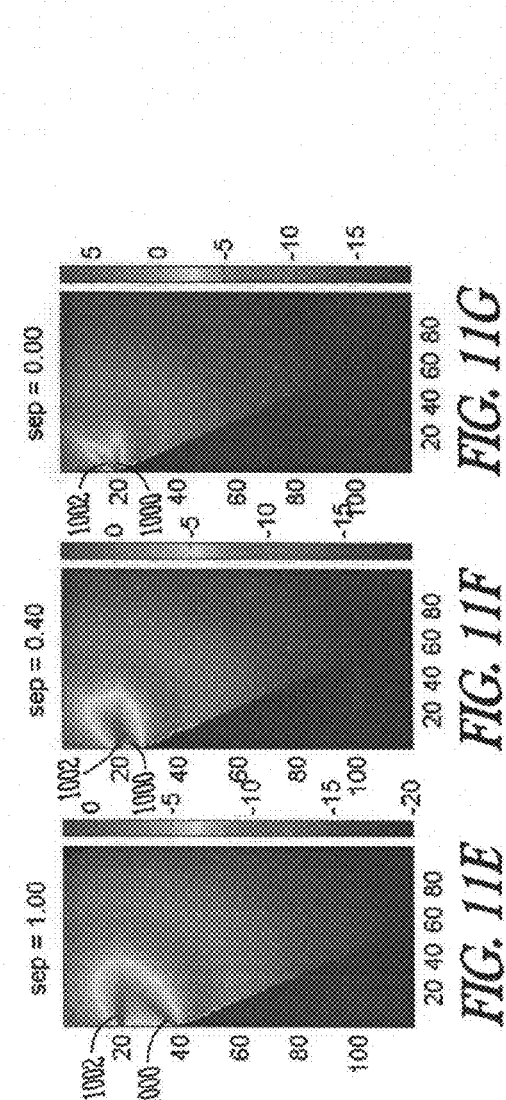

OPTICAL IMAGING OR SPECTROSCOPY SYSTEMS AND METHODS

CLAIMS OF PRIORITY

This patent application claims the benefit of priority, and is a continuation under 35 U.S.C. 111(a) of Elizabeth M. C. Hillman et al., PCT Patent Application No. PCT/US2008/008081, entitled OPTICAL IMAGING OR SPECTROSCOPY SYSTEMS AND METHODS, filed Jun. 27, 2008; which is incorporated by reference herein in its entirety, and through which priority is claimed to the following:
1. This patent application claims the benefit of priority, under 35 U.S.C. Section 119(e), to Elizabeth M. C. Hillman U.S. Provisional Patent Application Ser. No. 60/937,724, entitled "OPTICAL IMAGING OR SPECTROSCOPY SYSTEMS AND METHODS," filed on Jun. 29, 2007; which is incorporated herein by reference in its entirety;
2. This patent application claims the benefit of priority, under 35 U.S.C. Section 119(e), to Elizabeth M. C. Hillman et al. U.S. Provisional Patent Application Ser. No. 61/000,792, entitled "SIMULTANEOUS MULTI-WAVELENGTH LAMINAR OPTICAL TOMOGRAPHY IMAGING OF SKIN CANCER," filed on Oct. 29, 2007, which is incorporated herein by reference in its entirety; and
3. This patent application claims the benefit of priority, under 35 U.S.C. Section 119(e), to Elizabeth M. C. Hillman et al. U.S. Provisional Patent Application Ser. No. 61/130,904, entitled "DEPTH-RESOLVED OPTICAL IMAGING USING ARTICULATING ARM," filed on Jun. 4, 2008, which is incorporated herein by reference in its entirety.

STATEMENT REGARDING FEDERALLY SPONSORED RESEARCH OR DEVELOPMENT

This invention was made with government support under award number R21NS053684 from National Institute of Neurological Disorders and Stroke (NINDS), which is part of the National Institutes of Health (NIH). The government has certain rights in this invention.

Additional support was received from the Wallace H. Coulter Foundation.

BACKGROUND

There are both clinical and non-clinical applications for imaging an object of interest. In a clinical example, a body part may be imaged in two or three dimensions in various ways, such as by using radiation (e.g., X-ray or CT imaging), magnetism (e.g., magnetic resonance imaging), sound (e.g., ultrasound imaging), or light (e.g., optical coherence tomography). Spectroscopic information is also useful, such as for determining the composition of an object of interest.

OVERVIEW

The present inventors have recognized, among other things, that laser scanning microscopy can presently only achieve penetration depths of less than 600 μm, because of light scattering effects. Laser scanning microscopy also often uses an exogenous fluorescent contrast agent that is introduced into the object to enhance the resulting image. If three-dimensional (3D) images are to be acquired, laser scanning microscopy serially adjusts the focal plane of the light to sample different depths within the object, however, this can be time-consuming.

The present inventors have also recognized that laminar optical tomography (LOT) allows depth-resolved, non-contact imaging of an object such as living tissue at high frame rates, and such as to depths of greater than 2 mm with up to 100 to 200 μM resolution. Unlike laser scanning microscopy, LOT concurrently obtains information about various depths in parallel, rather than serially. LOT can image absorption contrast (such as oxyhemoglobin, deoxyhemoglobin, or melanin concentration) as well as fluorescence. For example, LOT can be applied to in-vivo dermal imaging of skin cancer or in-vivo imaging of the function of a rat brain. The LOT techniques can be performed at orthogonal or oblique angles, such as described further below.

The present inventors have further recognized that a technique of using LOT to acquire images at multiple wavelengths (e.g., so as to be able to distinguish between multiple different light-absorptive substances) can use respective shutters to modulate light from corresponding individual lasers emitting light at different wavelengths. However, the present inventors have also recognized that this can dramatically slow down image acquisition speed and can limit the number of wavelengths, types of light sources, or types of data that can be acquired.

Accordingly, the present inventors have recognized and developed a technique that allows multi-spectral LOT data to be acquired in parallel, such that data at one wavelength can be acquired concurrently with data at another (different) wavelength. Among other things, this means that multiple lasers—or even a broadband light source such as an LED or a lamp—can be used to concurrently illuminate the tissue with different wavelengths of light. Moreover, by a clever arrangement of the detection configuration, each wavelength can be distinguished and recorded concurrently—in addition to allowing the concurrent depth-resolved LOT data. In such a parallel or concurrent mode, image acquisition can proceed as fast as scanning of an incident beam allows. This can be quite fast and may generally merely be limited by galvanometer mirror scanning speed, digital data acquisition rate, or the noise floor of the light detector. Furthermore, discrete wavelength laser sources can be very expensive, and will typically provide only as many different distinct wavelengths as the number of lasers. By contrast, the present systems or methods permit use of one or more broadband sources or multi-wavelength lasers to potentially allow concurrent imaging of detailed depth-resolved spectral optical response information. For fluorescence imaging, the present systems or methods allow the full spectrum of the fluorescent emission to be measured, if desired. One or more excitation wavelengths can be used concurrently, while one or more different fluorophores can be measured and distinguished concurrently. Multiple concurrent measurements of the fluorescence emission spectrum can be recorded, allowing for spectroscopic analysis as well as imaging using the present techniques.

Thus, the present inventors believe that the present techniques can provide dramatic improvements to the efficacy, speed, and potential applications of LOT. Examples of potential applications include, without limitation, fluorescence and absorption contrast imaging or spectroscopy of living tissues, such as the brain, retina, skin, or endothelial tissues, such as the oral mucosa, colon, or cervix. By concurrently acquiring multi-spectral absorption or fluorescence measurements, rapid functional imaging can be accomplished.

The present inventors have also recognized that the present techniques can be used concurrently with diffuse correlation spectroscopy (DCS)—which can benefit from the scanning and other aspects of the present techniques. The DCS information can be used to directly or indirectly provide additional useful information, such as blood flow, tissue oxygenation, oxygen metabolism, or the like. This is particularly useful where the region of interest includes brain tissue, for example, such as for ischemia or stroke characterization. For example, absorption contrast can provide oxygenation information, which, combined with DCS, can yield metabolism information. Certain examples in this document describe a combined LOT/DCS system that is capable of concurrently quantifying (1) absorption (and hence oxyhemoglobin and deoxyhemoglobin dynamics in living tissue), (2) fluorescence (such as that from a calcium sensitive or voltage sensitive dye, a targeted molecular probe, or an intrinsic fluorophore such as FAD, NADH, or collagen), and (3) blood flow, such as via DCS.

The present inventors have further recognized that the present techniques can benefit from using an at least partially flexible optical conduit to communicate with the target region. For a human or animal subject, this can permit convenient external or internal imaging of a target location. In certain examples, such as for internal imaging of a body lumen, 360 degree circumferential viewing can be accomplished, such as by using a rotatable angled mirror. The rotatable angled mirror can also be useful in laparoscopic or oral examination, such as for examining the oral mucosa, for example. A specified separation between a distal portion of the optical conduit and the target region of the body can be obtained using an inflatable balloon or other fixed or adjustable separation device.

The present inventors have further recognized that one approach would be to use a LOT system that is built on a rigid platform, with optical components steering the laser beam or other light down onto the object to be imaged. The platform can be raised and lowered, and the objective lens can be tilted, but its utility can be severely restricted if imaging is to occur in the clinic where the face and neck are not easily and comfortably accessible via a rigid platform. Accordingly, the present inventors have recognized that, by introducing an articulating arm, and solving the associated optical and configuration difficulties of sending and detecting LOT or DCS signals, one can be enabled to image any area near which one can position the articulating arm. This can help extend all of the benefits of LOT or DCS to situations in which the LOT or DCS information is to be acquired in a clinic. In certain examples, the LOT or DCS system including the articulating arm can allow imaging of skin cancer lesions on the neck and face. The articulating arm can be used while still providing the LOT system with careful control over the off-axis returning light that allows depth-resolved LOT imaging (rather than just illumination). The articulating arm allows LOT or DCS to be extended to many more clinical applications than without the articulating arm, and can provide better signal-to-noise characteristics than an endoscopic embodiment. In certain examples, the LOT or DCS system including the articulating arm can be used in a non-medical imaging application, such as for example in industrial quality control in difficult to reach places (e.g., where depth-resolved imaging of turbid material is desirable). The articulating arm can also allow configurations that require delivered or detected light to retain one or more features that cannot be maintained during passage through an optical fiber. In certain examples, transmission of ultra-violet light, pulsed laser light, or polarized light can be significantly deteriorated by an endoscopic or other optical fiber conduit, as compared to an articulating arm including suitable reflectors, such as described further herein.

Example 1 can include subject matter that can comprise at least one light source providing at least one wavelength of light. In this example, the apparatus can comprise a scanner, configured to receive the light from the light source, and configured to scan a beam of the light across a target region. In this example, the apparatus can comprise a light detector, configured to receive from the target region a scanning response signal at a plurality of distances from a beam location upon the target region. In this example, the apparatus can comprise a wavelength separator, configured with respect to the light detector to direct a first wavelength of the scanning response signal to a different location of the light detector than a second wavelength of the scanning response signal, wherein the second wavelength is different from the first wavelength.

In Example 2, the subject matter of Example 1 can optionally comprise a signal processor, coupled to the light detector, the signal processor configured to concurrently process the scanning response signal of the first wavelength and the scanning response signal of the second wavelength. In this example, the lateral distances can define a linear first direction, and wherein the wavelength separator is configured to spatially separate wavelengths of the scanning response signal in a linear second direction that is orthogonal to the first direction.

In Example 3, the subject matter of any one of Examples 1 or 2 can optionally comprise the light detector including a two-dimensional array of light detector elements, and is configured to detect different wavelengths of the scanning response signal along a first dimension of the two-dimensional array, and to detect along a second dimension of the two-dimensional array optical responses from the different lateral distances from the beam location, and wherein the first and second dimensions of the two-dimensional array are orthogonal to each other, and comprising an imaging data memory including a two-dimensional array of memory locations for corresponding scanning locations of the target region, each two-dimensional array of memory locations storing data from the two-dimensional array of light detectors for a particular scanning location of the target region.

In Example 4, the subject matter of any one of Examples 1-3 can optionally comprise the light source comprising: a first laser, providing laser light at the first wavelength; and a second laser, providing laser light at the second wavelength that is different from the first wavelength, and wherein the first wavelength of the scanning response signal is in response to the first wavelength of laser light provided by the first laser, and wherein the second wavelength of the scanning response signal is in response to the second wavelength of laser light provided by the second laser.

In Example 5, the subject matter of any one of Examples 1-4 can optionally be configured such that the first wavelength of the scanning response signal is in response to a first emission wavelength of a first fluorophore, and wherein the second wavelength of the scanning response signal is in response to a second emission wavelength of a second fluorophore of the same type as the first fluorophore or of a different type than the first fluorophore.

In Example 6, the subject matter of any one of Examples 1-5 can optionally comprise a beam splitter configured to communicate light with the scanner and the wavelength separator.

In Example 7, the subject matter of any one of Examples 1-6 can optionally comprise a housing that carries at least the scanner and an objective lens.

In Example 8, the subject matter of any one of Examples 1-7 can optionally comprise a tubular spacer, configured to fit about the objective lens and to maintain a specified distance between the objective lens and the target region.

In Example 9, the subject matter of any one of Examples 1-8 can optionally comprise an articulating arm, configured to communicate light along the articulating arm, between the housing and the target region, without requiring a fiber optic conduit.

In Example 10, the subject matter of any one of Examples 1-9 can optionally be configured such that the articulating arm comprises: first and second elongated segments, each segment defining a longitudinal direction; a pivot, coupling the first and second elongated segments, wherein at least one of the first and second elongated segments is configured to rotate about the longitudinal direction with respect to the pivot; and wherein the pivot comprises an angled mirror configured to redirect light from along a longitudinal direction of a first segment to be along a longitudinal direction of the second segment.

In Example 11, the subject matter of any one Examples 1-10 can optionally comprise at least two pivots and at least three segments.

In Example 12, the subject matter of any one of Examples 1-11 can optionally be configured such that the light source comprises a broadband light source.

In Example 13, the subject matter of any one of Examples 1-12 can optionally be configured such that the wavelength separator includes at least one of a prism, a diffraction grating, a dichroic filter, or multiple dichroic mirrors.

In Example 14, the subject matter of any one of Examples 1-13 can optionally be configured such that the wavelength separator receives light from a slit that defines a longitudinal direction such that the plurality of lateral distances from the beam location upon the target region correspond to different locations along the longitudinal direction of the slit.

In Example 15, the subject matter of any one of Examples 1-14 can optionally comprise: a correlator circuit, coupled to the light detector to receive and compute a temporal correlation of the scanning response signal from the target region; and a signal processor, configured to receive and use the temporal correlation to compute a first characteristic of the target region.

In Example 16, the subject matter of any one of Examples 1-15 can optionally comprise the signal processor configured to receive, in response to the same scanning, a fluorescence component of the scanning response signal, and to use the fluorescence component of the scanning response signal to compute a second characteristic of the target region.

In Example 17, the subject matter of any one of Examples 1-16 can optionally comprise the signal processor being configured to receive, in response to the same scanning, an absorption component of the scanning response signal, and to use the absorption component of the scanning response signal to compute a third characteristic of the target region.

In Example 18, the subject matter of any one of Examples 1-17 can optionally comprise the signal processor being configured to receive, in response to the same scanning, an absorption component of the scanning response signal, the absorption component comprising at least two different wavelengths of light, and to use the absorption component of the scanning response signal to compute the third characteristic of the target.

In Example 19, the subject matter of any one of Examples 1-18 can optionally comprise: an optical conduit, optically coupled to the scanner and the light detector, the optical conduit configured to communicate the beam of the first wavelength of light to the target region, and configured to communicate the scanning response signal from the target region; and a laparascopic or endoscopic instrument carrying the optical conduit.

In Example 20, the subject matter of any one of Examples 1-19 can optionally be configured such that a distal portion of the conduit includes a longitudinal-to-side optical translator guide that comprises a mirror that is obliquely angled with respect to a longitudinal axis of the optical conduit.

In Example 21, the subject matter of any one of Examples 1-20 can optionally be configured such that the mirror is rotatable about the longitudinal axis of the optical conduit.

Example 22 can include, or can be combined with any one of Examples 1-21 to optionally include, subject matter including: sourcing light to form an incident beam; scanning a location of the incident beam across a target region; obtaining an optical response at different locations at different distances in a first direction from the beam location upon the target region; dispersing different wavelengths of the optical response; and detecting the dispersed wavelengths of the optical response from the different locations concurrently to provide information about the target region.

In Example 23, the subject matter of any one of Examples 1-22 can optionally be configured such that sourcing the light includes sourcing light at different wavelengths.

In Example 24, the subject matter of any one of Examples 1-23 can optionally be configured such that detecting the dispersed wavelengths of the optical response includes detecting a first and second wavelengths of fluorophore emission, wherein the first wavelength of fluorophore emission is different from the second wavelength of fluorophore emission.

In Example 25, the subject matter of any one of Examples 1-24 can optionally be configured such that detecting the dispersed wavelengths of the optical response includes detecting the first wavelength of fluorophore emission from a first type of fluorophore and detecting the second wavelength of fluorophore emission from a second type of fluorophore that is different from the first type of fluorophore.

In Example 26, the subject matter of any one of Examples 1-25 can optionally be configured such that dispersing different wavelengths of the optical response includes dispersing along a linear second direction that is orthogonal to the first direction at a light detector.

In Example 27, the subject matter of any one of Examples 1-26 can optionally comprise: storing a two-dimensional array of response information from the light detector for different beam locations of the target region; and using the stored two-dimensional array of response information from the light detector for different beam locations of the target region to construct at least one of: a three dimensional rendered image of the target region; an image representing chemical composition of the target region; and a plurality of images representing information about different depths of the target region.

In Example 28, the subject matter of any one of Examples 1-27 can optionally be configured such that dispersing different wavelengths comprises refracting different wavelengths by different amounts.

In Example 29, the subject matter of any one of Examples 1-28 can optionally be configured such that dispersing different wavelengths comprises diffracting the different wavelengths by different amounts.

In Example 30, the subject matter of any one of Examples 1-29 can optionally be configured such that dispersing different wavelengths includes filtering a first wavelength from a second wavelength.

In Example 31, the subject matter of any one of Examples 1-30 can optionally comprise: computing, for the multiple different lateral locations, a temporal correlation of the scanning optical response; and computing a first characteristic of the target region using the temporal correlation.

In Example 32, the subject matter of any one of Examples 1-31 can optionally comprise obtaining, in response to the same scanning, a fluorescence component of the scanning optical response signal; and using the fluorescence component of the scanning optical response signal to compute a second characteristic of the target region.

In Example 33, the subject matter of any one of Examples 1-32 can optionally comprise obtaining, in response to the same scanning, an absorption component of the scanning optical response signal; and using the absorption component of the scanning optical response signal to compute a third characteristic of the target region.

In Example 34, the subject matter of any one of Examples 1-33 can optionally comprise obtaining, in response to the same scanning, an absorption component of the scanning optical response signal, the absorption component comprising at least two different wavelengths of light; and using the absorption component of the scanning optical response signal to compute a third characteristic of the target region.

In Example 35, the subject matter of any one of Examples 1-34 can optionally comprise using an optical conduit to communicate light to and from the target region.

In Example 36, the subject matter of any one of Examples 1-35 can optionally comprise scanning an incident beam location and obtaining an optical response are carried out for a target location that is internal to a human or animal.

In Example 37, the subject matter of any one of Examples 1-36 can optionally be configured such that scanning an incident beam location and obtaining an optical response are carried out for a target location that is orthogonal to a longitudinal axis of the optical conduit.

In Example 38, the subject matter of any one of Examples 1-37 can optionally comprise: scanning the location of the incident beam across a target region comprising skin; and using the information about the target region to discriminate between first and second skin conditions.

In Example 39, the subject matter of any one of Examples 1-38 can optionally comprise using an oblique angle from the target region for at least one of the scanning or the obtaining the optical response.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 10A is a color plot of modeled data indicating probability of light passing through various regions of tissue, a separation distance of 3.00 mm between incident light (at a 15 degree angle from a line perpendicular to the tissue surface) and a location at which the optical response is observed.

FIG. 10B is a color plot of modeled data indicating probability of light passing through various regions of tissue, a separation distance of 2.50 mm between incident light (at a 15 degree angle from a line perpendicular to the tissue surface) and a location at which the optical response is observed.

FIG. 10C is a color plot of modeled data indicating probability of light passing through various regions of tissue, a separation distance of 2.00 mm between incident light (at a 15 degree angle from a line perpendicular to the tissue surface) and a location at which the optical response is observed.

FIG. 10D is a color plot of modeled data indicating probability of light passing through various regions of tissue, a separation distance of 1.00 mm between incident light (at a 15 degree angle from a line perpendicular to the tissue surface) and a location at which the optical response is observed.

FIG. 10E is a color plot of modeled data indicating probability of light passing through various regions of tissue, a separation distance of 0.50 mm between incident light (at a 15 degree angle from a line perpendicular to the tissue surface) and a location at which the optical response is observed.

FIG. 10F is a color plot of modeled data indicating probability of light passing through various regions of tissue, a separation distance of 0.20 mm between incident light (at a 15 degree angle from a line perpendicular to the tissue surface) and a location at which the optical response is observed.

FIG. 10G is a color plot of modeled data indicating probability of light passing through various regions of tissue, a separation distance of 0.00 mm between incident light (at a 15 degree angle from a line perpendicular to the tissue surface) and a location at which the optical response is observed.

FIG. 11A is a color plot of modeled data indicating probability of light passing through various regions of tissue, a separation distance of 4.00 mm between incident light (at a 35 degree angle from a line perpendicular to the tissue surface) and a location at which the optical response is observed.

FIG. 11B is a color plot of modeled data indicating probability of light passing through various regions of tissue, a separation distance of 3.00 mm between incident light (at a 35 degree angle from a line perpendicular to the tissue surface) and a location at which the optical response is observed.

FIG. 11C is a color plot of modeled data indicating probability of light passing through various regions of tissue, a separation distance of 2.00 mm between incident light (at a 35 degree angle from a line perpendicular to the tissue surface) and a location at which the optical response is observed.

FIG. 11D is a color plot of modeled data indicating probability of light passing through various regions of tissue, a separation distance of 1.50 mm between incident light (at a 35 degree angle from a line perpendicular to the tissue surface) and a location at which the optical response is observed.

FIG. 11E is a color plot of modeled data indicating probability of light passing through various regions of tissue, a separation distance of 1.00 mm between incident light (at a 35 degree angle from a line perpendicular to the tissue surface) and a location at which the optical response is observed.

FIG. 11F is a color plot of modeled data indicating probability of light passing through various regions of tissue, a separation distance of 0.40 mm between incident light (at a 35 degree angle from a line perpendicular to the tissue surface) and a location at which the optical response is observed.

FIG. 11G is a color plot of modeled data indicating probability of light passing through various regions of tissue, a separation distance of 0.00 mm between incident light (at a 35 degree angle from a line perpendicular to the tissue surface) and a location at which the optical response is observed.

DETAILED DESCRIPTION

Optical imaging or spectroscopy described can use laminar optical tomography (LOT), diffuse correlation spectroscopy (DCS), or the like. An incident beam is scanned across a target. In various examples, time-resolved (e.g., pulsed light) can be used, such as to obtain fluorescence lifetime or scattering information. Frequency modulated light can be used, in certain examples. Cross-polarized or other polarized light can be used, in certain examples. An optical response to the incident beam can be obtained, such as concurrently at different distances from the incident beam. Such different distances can be linearly displaced from the incident beam, circumferentially displaced from the incident beam, or displaced in orthogonal directions from the incident beam location, in various examples. The optical response from multiple incident wavelengths can be concurrently obtained by dispersing the response wavelengths in a direction orthogonal to the response distances from the incident beam. Temporal correlation can be measured, from which flow and other parameters can be computed. An optical conduit can enable endoscopic or laparoscopic imaging or spectroscopy of internal target locations. An articulating arm can communicate the light for performing the LOT, DCS, or the like. The imaging can be used for skin cancer diagnosis, such as distinguishing lentigo maligna (LM) from lentigo maligna melanoma (LMM).

Figure 1:
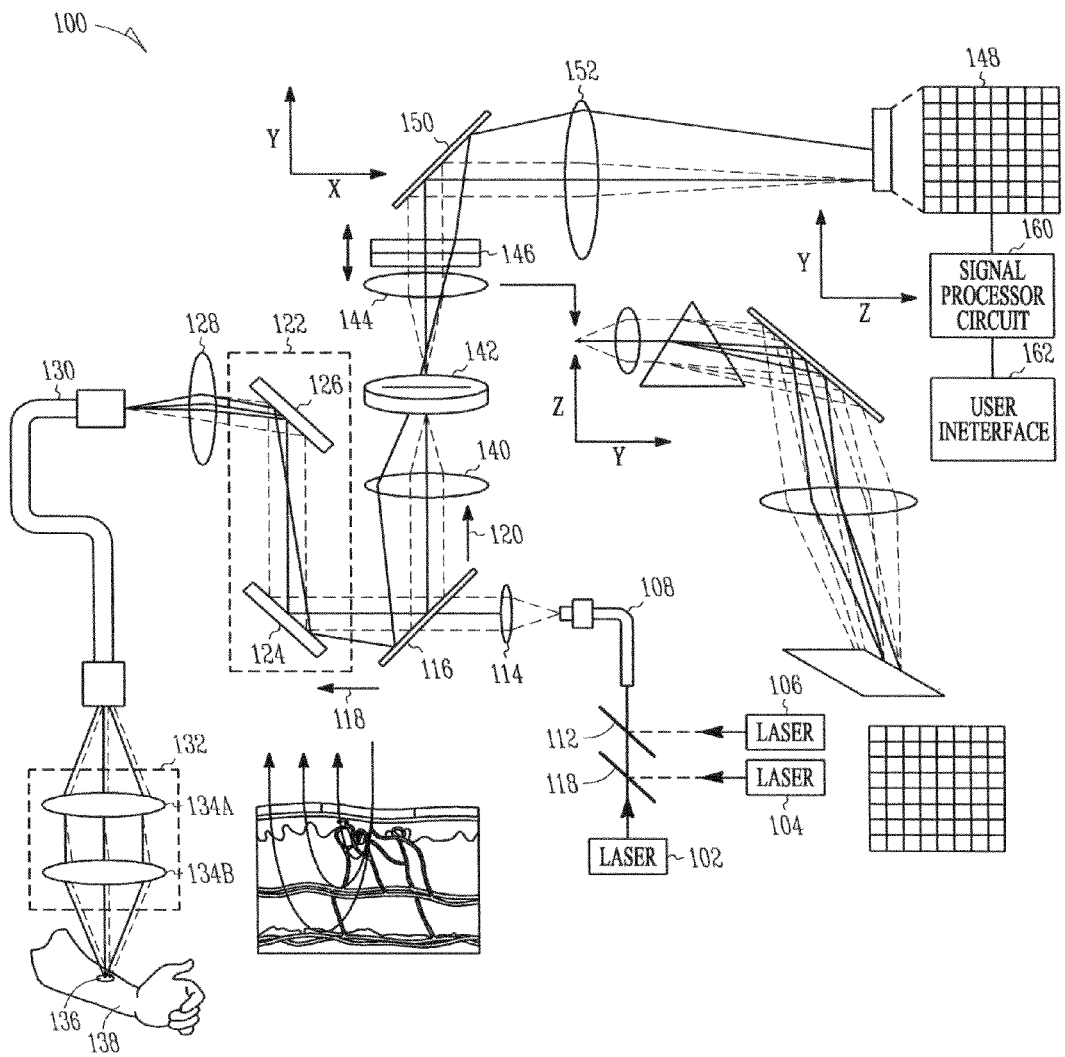
FIG. 1 is a schematic diagram illustrating generally portions of a system for optical imaging or spectroscopy and portions of an environment in which the system can be used.

FIG. 1 is a schematic diagram illustrating generally portions of a system 100 for optical imaging or spectroscopy and portions of an environment in which the system 100 can be used. In this illustrative example, the system 100 can include at least one light source, such as one or more of lasers 102, 104, or 106 providing laser light having at least two different light emission wavelengths. In the illustrative example of FIG. 1, the laser 102 emits 635 nm light, the laser 104 emits 532 nm light, and the laser 106 emits 473 nm light. In this example, the light from the multiple light sources of the lasers 102, 104, and 106 can be combined and delivered to an optional optical conduit, such as an optical fiber conduit 108 of one or multiple optical fibers. In this example, in which three different wavelengths of light are shown for illustrative purposes, the combining of the different wavelengths of light can be accomplished using a first frequency/wavelength selective filter (e.g., a 45° angled dichroic mirror 110) and a second frequency/wavelength selective filter (e.g., a 45° angled dichroic mirror 112). In this example, the dichroic mirror 110 passes light having wavelengths longer than 600 nm (such as the 635 nm light from the laser 102) and reflects shorter wavelengths (such as the 532 nm light from the laser 104). In this way, the dichroic mirror 110 can be used to combine the different-wavelength light from the lasers 102 and 104. In this example, the dichroic mirror 112 passes light having wavelengths longer than 500 nm (such as the 635 nm light from the laser 102 and the 532 nm light from the laser 104) and reflects shorter wavelengths (such as the 473 nm light from the laser 106). In this way, the dichroic mirror 112 can be used to combine the different wavelength light from the lasers 102, 104, and 106.

In the example of FIG. 1, the optical fiber conduit 108 delivers the combined different wavelength light from the lasers 102, 104, and 106 to a refractive element, such as a lens 114. The lens 114, in turn, collimates and delivers the combined different wavelength light to a beam-splitter, such as the polarizing beam splitter 116. In this example, the beam splitter 116 provides a first portion of this light along a first path 118 toward the object to be imaged. This beam splitter 116 can also serve to direct light returning from the object to be imaged along a second path 120 toward an imaging detector apparatus, such as described further below.

In the example of FIG. 1, the light provided along the first path 118 is delivered to an optical scanner 122. In this example, the scanner 122 scans its received light across various locations on a two-dimensional x-y plane. To accomplish this, the scanner 122 can include an x-scanner galvanometer 124 and a y-scanner galvanometer 126, each of which can be computer controlled. Other techniques of scanning or otherwise steering the light can include using an acousto-optical deflector, a polygonal scanning mirror arrangement, a microelectromechanical (MEMs) mirror array, or any other suitable light steering technique. In this example, the x-y scanned beam of light that is output by the scanner 122 can be provided to a refractive element, such as a lens 128, which focuses the scanned light beam at a desired location on a proximal end portion of a flexible optical conduit 130, such as an optical fiber bundle. In this example, a distal end portion of the flexible optical conduit 130 provides the light to a variable magnifier 132. The variable magnifier 132 can include first and second refractive elements 134A-B, having a variable distance with respect to each other or to the distal end portion of the optical conduit 130. The variable magnifier 132 can serve as an objective lens that permits scanning its incident light beam across a larger (or smaller) field of view, to permit receiving an optical response signal across the larger (or smaller) field of view. The variable magnifier 132 can also serve to adjust the effective separation between the incident light beam and the detected optical response signal. This allows adjustment of the depth of penetration of the incident light beam that is represented by the detected optical response signal. It also allows adjustment of the depth resolution represented by the detected optical response signal. The variable magnifier 132 need not be located at or near the distal end portion of the optical conduit 130, but can alternatively be located at or near the proximal end of the optical conduit 130, or to an intermediate portion of the optical conduit 130, or the variable magnifier 132 can be omitted altogether, if desired. In certain examples, the lenses 140, 144, or 152 can be adjusted to change the separation between the "source" and "detector" light, such as independent of the field of view.

In the example of FIG. 1, the light is delivered to an object to be imaged, such as, for example, a skin lesion site 136 on a person's arm 138. An optical response signal can be detected and communicated back along the first path 118 to the beam splitter 116, and then along the second path 120 toward an imaging detector apparatus, such as described further below. This optical response signal can include information about one or more of absorbed light (e.g., at the same wavelength as the incident light), reflected light (e.g., at the same wavelength as the incident light), or a fluorescence light emission (e.g., at a different wavelength than the incident light). The optical response signal need not occur at the particular location of incidence at which the scanned incident light was delivered. Instead, nearby locations can emit a response signal, with locations that are laterally more distant from the light beam's incident location at the site 136 generally providing an optical response associated with incident light that has traveled more deeply into the object to be imaged. Thus, the distance between the location of the emitted optical response signal and the location of the incident light is indicative of the depth to which the incident light has traveled. Analyzing the optical response signal at multiple such varying distances from the location of incidence permits depth-resolved non-contact imaging of living tissue, which can be referred to as a form of laminar optical tomography (LOT), such as described herein, such as to depths of greater than 2 mm with resolution on the order of about 100 to 200 μm, depending on tissue type. The reconstruction analysis can be performed using modeling such as Monte Carlo simulation, such as described below.

The second path 120 receives light from the beam-splitter 116. In this illustrative example, a refractive element, such as a lens 140, focuses the light onto an input of an element comprising a slit 142. An output of the slit 142 provides the light to a refractive element, in this example, such as the lens 144. However, at this point, the optical response light signal does not separate information according to wavelength. One approach to separate information by wavelength is to provide a shuttering mechanism to provide light of a particular wavelength, then analyze the response from that wavelength, and repeat in a time sequence for other wavelengths. However, shuttering is time-consuming such that it is possible that a biological change can occur before all wavelengths of light are provided and their responses observed. In the case of such an intervening biological change, the multiple wavelengths and their responses can fail to provide a unique spectroscopic solution, can involve using more sophisticated detection components, or can be slow.

The present inventors have recognized, among other things, that a wavelength separator such as a dispersive element 146 can be used in a clever arrangement to solve this problem. In this example, the lens 144 collimates and provides the light via a slit to the dispersive element 146, such as to a prism, diffraction grating, or one or more dichroic filters. The slit can be arranged in a first direction (e.g., a y-direction) such that distances along a length of the slit represent the various lateral distances, from the location of instance of the incident light, at which the optical response signal is observed. The present inventors have recognized, among other things, that the dispersive element 146 can be used to disperse the different wavelengths of the response signal in a second direction (e.g., an "x" direction) that is orthogonal to the first direction of the slit. The resulting x-y array of wavelength vs. lateral distance optical response information from the dispersive element 146 can be captured using a light detector, such as an x-y photomultiplier array 148, a charge-coupled device (CCD) light detector array, a photodiode array, or a square optical fiber bundle or collection of linear fiber or detector arrays.

In the example of FIG. 1, a reflective element, such as a mirror 150, can optionally be used to direct the light from the dispersive element 146 and toward a refractive element, such as a lens 152. The lens 152 can be used to provide variable magnification, such as to adjust the x-y dispersion provided by the dispersive element 146 to more fully use the space provided by the x-y photomultiplier array 148, thereby increasing or maximizing its spectral resolution. Information from the 2D light detector array 148 is provided to a computer-implemented or other signal processor circuit 160 to perform desired computation or analysis, such as the Monte Carlo model-based reconstruction described below. The signal processor circuit 160 can communicate with a user interface 162, which can include a display, such as to provide information obtained using the desired computation or analysis.

LOT using a single wavelength of incident light provides depth-resolved optical imaging information. By including the dispersive element 146 in the LOT system 100, such multiple different wavelengths can be used concurrently, and the resulting optical response information can be concurrently separated according to such different wavelengths. Such wavelength-separated information can then be processed, such as to generate a rendered volumetric image or to perform spectroscopic analysis of the composition of the object being examined. Concurrent use of different wavelengths allows faster imaging or spectroscopy. Information acquisition speed is particularly important for imaging or spectroscopy of biological targets, in which the target otherwise might undergo a change during the time between imaging or spectroscopy of first and second different wavelengths, which could potentially render a slower (e.g., serially-obtained) composite of such information useless. Moreover, the present inventors have recognized that concurrent use of different wavelengths allows use of different light sources. In certain examples, a cheaper broadband light source (e.g., a light-emitting diode (LED) or a lamp) can replace the laser light sources described above, since the resulting information can be spectrally separated such as described above. Thus, even though FIG. 1 illustrates an example in which three different distinct wavelengths of light are used, other examples can use fewer distinct wavelengths, (e.g., 2 wavelengths), more distinct wavelengths (e.g., 4, 5, 6, . . . , etc. wavelengths), or even more wavelengths that are not necessarily distinct, such as a broadband light source, for example. Thus, FIG. 1 is merely an illustrative example; not all components illustrated in FIG. 1 are required in all examples. Moreover, the present approach using the spectral dispersion of concurrent multiple wavelengths could be cheaper than temporal sequencing of different wavelengths using expensive shutters and separate lasers for each wavelength; instead, an unshuttered less expensive single laser concurrently emitting multiple wavelengths of light can be used, for example.

The present approach can also be useful for observing an exogenous or endogenous fluorescence response, such as in tissue. In an exogenous approach, a contrast agent, which can include multiple fluorophores that emit a fluorescence response at different wavelengths, can be introduced into the tissue. In an endogenous approach, an intrinsic fluorophore emits the fluorescence response at a different wavelength than the excitation wavelength. In either an exogenous or endogenous approach, a single excitation wavelength (or even a broadband light source) can be used to obtain the fluorescent emission response. The optical response at the excitation wavelength can be notch-filtered or otherwise attenuated or removed from the optical response information, such as for emphasizing the fluorescent emission relative to the optical response at the excitation wavelength.

The multiple fluorescence emission bands (e.g., from Nicotinamide adenine dinucleotide (NADH), flavin adenine dinucleotide (FAD), collagen, elastin, a calcium-sensitive or voltage sensitive dye, as an illustrative example) can be spectrally separated using the dispersive element 146, and detected using a 2 dimensional light detector array, or a series of stacked 1 dimensional linear light detector arrays, for example. In certain examples, information from the 2D light detector array 148 can be used to measure light scattering in two orthogonal directions (e.g., in an L-shape, rather than along a line). This may provide useful information about the tissue, such as information about the scattering anisotropy.

Figure 2:
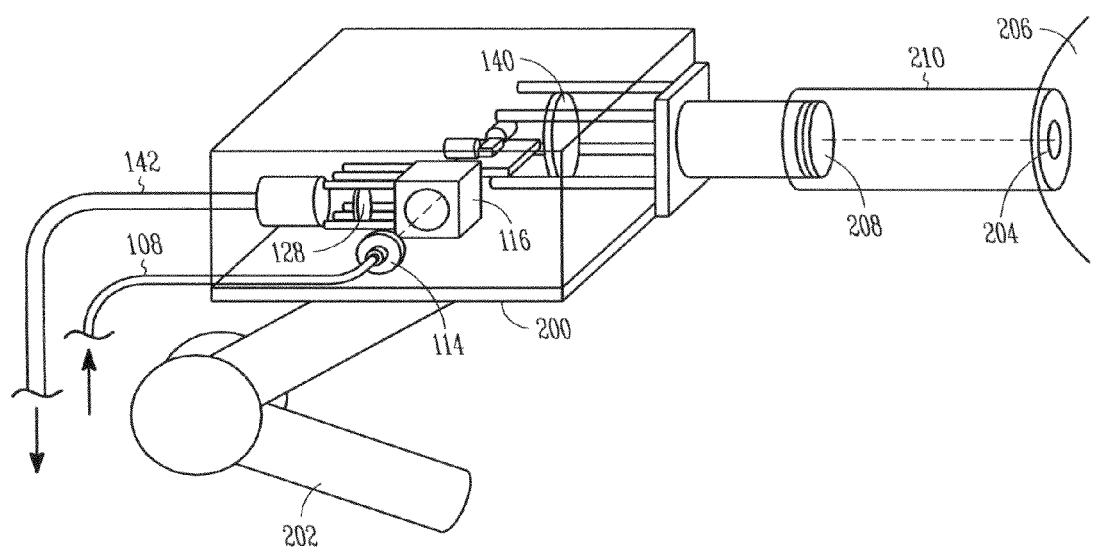
FIG. 2 is a schematic drawing illustrating generally an example of an interface apparatus, such as for the system illustrated in FIG. 1.

FIG. 2 is a schematic drawing illustrating generally an example of an interface apparatus, such as for the system 100 illustrated in FIG. 1. In the illustrative example of FIG. 2, a housing 200 can be mounted onto an articulated arm 202, such that the location of the housing 200 can be manually, robotically, or automatically manipulated with respect to a target object to be imaged, such as an external skin lesion 204 on a patient 206, for example. The housing 200 can house at least some of the components illustrated in FIG. 1, such as the lens 114, the polarizing beam splitter 116, the x-scanner galvanometer 124 the y-scanner galvanometer 126, the lens 128, and the lens 140. The optional objective lens 208 can include the variable magnification lenses 134A-B of FIG. 1, such as in an example in which it is desirable to adjust the beam size upon the object, the field of view, or the effective separation between incident light and the detected optical response light. An optional hollow tube 210 of a specified length (e.g., 150 mm) can be fitted to the objective lens 208 or to the housing 200 to help provide and maintain a consistent desired spacing between the objective lens and the object to be imaged. The tube 210 can be at least partially opaque, such as to the wavelengths of light used in the imaging, such as to help protect a user or subject from exposure to stray laser light, for example. The tube 210 can be transparent to other portion(s) of the visible spectrum, if desired, so as to allow the user to visualize the target 204. Spacing apart from the target tissue is not required. In another example, a distal portion of the apparatus is pressed directly against the target tissue, which may help reduce motion artifact. Such a mechanism can also include a safety interlock, in certain examples, such as to inhibit or prevent accidental exposure to laser radiation. A disposable (e.g., transparent) plastic barrier can be used so that the apparatus need not be cleaned between uses with different patients.

Figure 3:
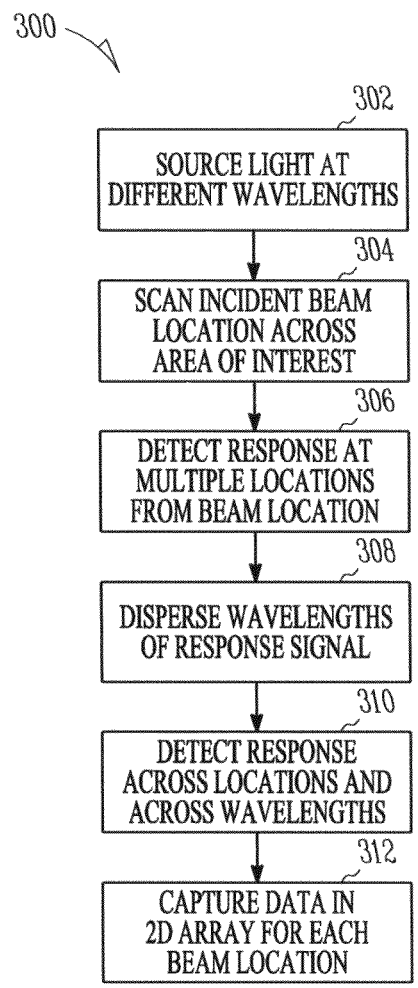
FIG. 3 is a diagram illustrating generally an example of a method that permits concurrently obtaining and separating depth-resolved and spectrally-resolved laminar optical tomography information, such as for use in imaging or spectroscopy.

FIG. 3 is a diagram illustrating generally an example of a method 300 that permits concurrently obtaining and separating depth-resolved and spectrally-resolved laminar optical tomography information, such as for use in imaging or spectroscopy. At 302, light is sourced at two or more different wavelengths, which can be either distinct individual wavelengths or a broader spectrum of wavelengths. For example, this can include incident light at 635 nm, 532 nm, and 473 nm, such as illustrated in FIG. 1. At 304, an incident beam location is scanned across an imaging area of interest. For example, this can include using an x-galvanometer and a y-galvanometer, such as described with respect to FIG. 1. At 306, an optical response to the incident light can be detected at multiple locations, such as at different lateral distances from the incident beam location being scanned at that particular time. At 308, the constituent wavelengths of the optical response are dispersed, such as across a linear dimension. This linear dimension across which these wavelengths are dispersed can be arranged to be orthogonal to a linear dimension of the different locations at which the incident light is detected at 306. At 310, the optical response to the incident light is detected across the different locations and across the different wavelengths. For example, this can include using a two-dimensional optical detector such that the different locations are dispersed across a first direction (e.g., an x-direction) and the different wavelengths are dispersed across a second direction (e.g., a y-direction) that is orthogonal to the first direction. At 312, the resulting detected response data can be stored, such as in a two-dimensional memory array with memory locations corresponding to the different locations in the two-dimensional optical detector used at 310. As the incident beam is scanned across different scanning locations of the imaging region of interest, a two-dimensional array of response data can be detected and stored for each such scanning location. The data can be used for producing a rendered volumetric image, or for performing spectroscopy analysis (e.g., using the object's spectral absorption or fluorescence profile), such as to determine the volumetric composition of the object.

Figure 4:
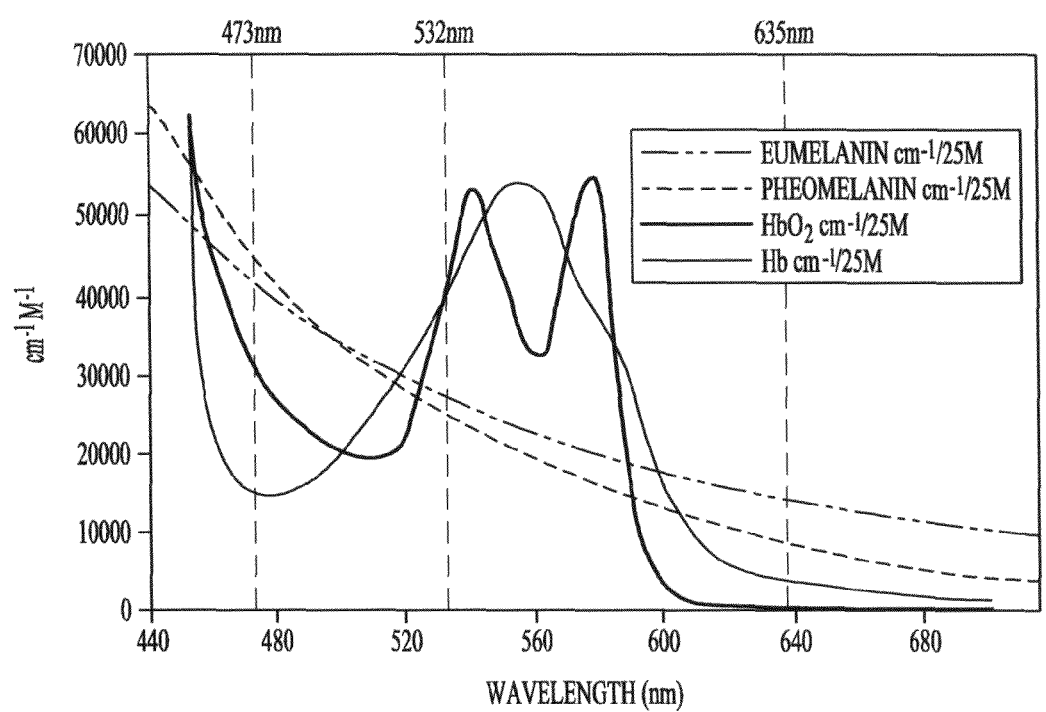
FIG. 4 is an example of a plot of absorption vs. wavelength for melanin, HbO2, and HbR.

Thus, in certain examples, the above system 100 and method 300 can use a two-dimensional detector array, multiple linear detector arrays, or multiple linear detectors, along with a diffraction grating, prism, or other spectrally separating optical element to concurrently image multi-spectral on-axis or off-axis scattered light from a scanning spot to allow depth-resolved optical imaging or spectroscopy. For example, the two-dimensional detector array is useful for performing multi-spectral LOT imaging or spectroscopy. The linear array is useful for DCS. The above system 100 and method 300 are advantageous over a system and method that uses serial illumination of different wavelengths of laser light, and either multiple individual detectors or a linear array of detectors. Serial illumination of different wavelengths of light typically involves a complicated shuttering process. It will therefore result in slower imaging frame rates, and can result in a lack of simultaneity in measurements of living dynamic systems (e.g., movement artifacts or fast hemodynamic changes can inhibit quantitative spectroscopic analysis of results). Examples of some applications of the present systems and methods include, without limitation, fluorescence, absorption, or scattering contrast imaging or other spectroscopy of living tissues, such as the brain, retina, skin, or endothelial tissues such as the oral mucosa, colon, or cervix. By having concurrently acquired multi-spectral absorption or fluorescence measurements, rapid functional imaging can be accomplished. Multi-spectral detection allows separation of signals, such as from mixtures of fluorophores or chromophores, such as voltage or calcium sensitive dyes, molecular probes, collagen, NADH, flavoproteins, tryptophan, oxyhemoglobin, deoxyhemoglobin, melanin, lipid, water, cytochrome, etc. For example, FIG. 4 is an example of a plot of absorption vs. wavelength for melanin, HbO2, and HbR, demonstrating that the laser wavelengths described with respect to FIG. 1 can provide measurements for achieving spectral separation. As an illustrative example, if spectral information at three wavelengths is acquired, and spectral response information about three substances is known, this permits simultaneous solving of three equations of three variables, such as to obtain information about concentrations of the three substances. Thus, there are considerable advantages to the ability of the present systems and methods to efficiently combine both multi-spectral and depth-resolved imaging or spectroscopy data, and the present systems and methods are not limited to dermal imaging or spectroscopy, but can also be used in other applications such as, for example, brain imaging, or non-clinical or non-biological applications.

Figure 5:
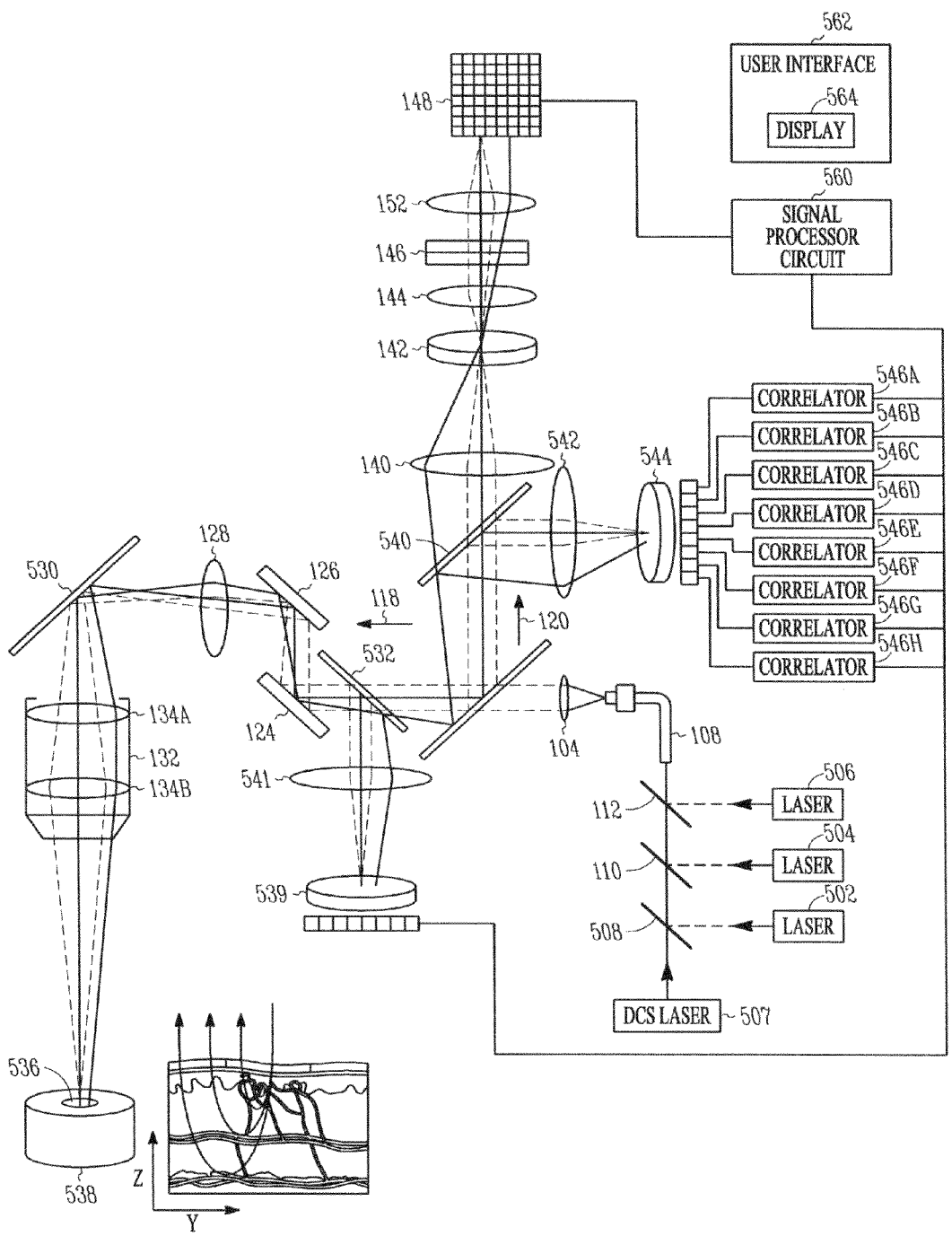
FIG. 5 is a schematic drawing illustrating generally an example of a system, such as for concurrently performing LOT and diffuse correlation spectroscopy (DCS).

FIG. 5 is a schematic drawing illustrating generally an example of a system 500, such as for concurrently performing LOT and diffuse correlation spectroscopy (DCS). As described above, LOT can be configured to concurrently provide both spectrally-resolved and depth-resolved imaging or spectroscopy data, such as by scanning an incident light beam across a tissue or other region of interest, and using optical response information such as absorption or fluorescence. The present inventor has also recognized that by concurrently performing DCS, blood flow or other useful information can also be obtained, such as concurrently obtained along with the LOT data. This is useful, as an illustrative example, in a brain imaging application such as for determining whether ischemia is present, such as resulting from a stroke, for example.

DCS generally involves using a laser source for providing incident light, such as at a wavelength that typically exhibits a desired coherence length over which the incident light maintains a desired degree of coherence. Light scattering by the tissue or other target object can be detected. Fluctuations in the detected scattered light can be ascertained, such as by using a correlator circuit or like module to compute one or more temporal correlation statistics of the detected scattered light. In tissue having blood flow, such as a region of interest of the brain, for example, less blood flow will result in a longer time-constant of temporal correlation of the detected scattered light. Conversely, more blood flow will result in a shorter time-constant of temporal correlation of the detected scattered light. Information about blood flow or changes in blood flow is useful by itself. Moreover, such information can also be used, for example, in determining tissue oxygenation, tissue oxygen extraction, or tissue oxygen metabolism. DCS information can also be used to generate 3D imaging information, such as described further below.

FIG. 5 is similar to FIG. 1 in certain respects. In the example of FIG. 5, laser light sources 502, 504, and 506 are similar to the laser light sources 102, 104, and 106 of FIG. 1. In the example of FIG. 5, the light source 502 emits laser light at a wavelength 636 nm, the light source 504 emits laser light at a wavelength of 532 nm, and the light source 506 emits laser light at a wavelength of 488 nm. This example also includes a light source 507 that emits light having a desired coherence length for performing DCS. In this example, the laser light source 507 emits laser light at a wavelength of 800 nm, which can permit using the desired coherence length for performing DCS.

In this example, the different wavelengths of light from the corresponding different lasers 502, 504, 506, and 507 are combined and delivered to the lens 104, either directly or such as via an optional optical fiber conduit 108. In certain examples, such as for providing light for performing DCS, a single-mode low dispersion optical fiber conduit 108 is used. In this example, in which four different wavelengths of light are shown for illustrative purposes, the combining of the different wavelengths of light can be accomplished similarly to that described above with respect to FIG. 1, but including an additional frequency selective filter (e.g., a 45° angled dichroic mirror 508). The dichroic mirror 508 passes light having wavelengths longer than 700 nm (such as the 800 nm light from the laser 507) and reflects shorter wavelengths (such as the 636 nm light from the laser 502).

The light from the light sources 502, 504, 506, and 507 is delivered to the optical fiber or other optical conduit 108 and, similarly to the above description with respect to FIG. 1, is delivered to a site of interest 536 in an object of interest 538, such as a brain region, for example. In the schematic drawing of FIG. 5, a mirror 530 is used in place of the optical conduit 130 of FIG. 1, however, the optical conduit 130 of FIG. 130 of FIG. 1 could be used in FIG. 5 instead of the mirror 530, and vice-versa. FIG. 5 also includes a frequency selective filter 532 (e.g., one or more 45° angled dichroic mirrors). The frequency selective filter 532 passes light having the same wavelengths as the incident light lasers 502, 504, 506, and 507 (e.g., passes light at wavelengths of 636 nm, 532 nm, 488 nm, and 800 nm, in this example). However, the frequency selective filter 532 reflects light at other wavelengths, such as the fluorescence components of the optical response to these incident light wavelengths. In this way, the fluorescence optical response signal can be extracted and provided to a light detector 539. This can be carried out via a refractive element, for example, such as a lens 541 that focuses the light on a desired region of the light detector 539. In this example, the light detector 539 includes an at least one-dimensional (1D) array of individual light detecting elements, such as a 1D photomultiplier array, and the resulting information can be provided to a signal processor circuit 560. This permits resolving the fluorescence signal from different lateral locations at the site 536 with respect to the location of the incident light beam. As discussed above, such different lateral locations represent responses from light that has penetrated to different depths of the object 538; responses obtained at more distant lateral locations are presumed to have penetrated into the object 538 more deeply. Using a light propagation model, such information can be used to generate a 3D volumetric image representation of the fluorescence optical response. The absorption optical response can be detected using the light detector 148, such as described above with respect to FIG. 1, with the resulting information provided to a signal processor circuit 560 to perform desired computation or analysis. The signal processor circuit 560 can communicate with a user interface 562, which can include a display 564, such as for displaying rendered or other imaging information, spectroscopy information, or the like.

FIG. 5 also includes another wavelength selective optical filter (e.g., a 45° angled dichroic mirror 540). In this example, the dichroic mirror 540 passes light having wavelengths shorter than 750 nm and reflects light having longer wavelengths. In this way, the optical response to the 800 nm DCS laser 507 can be extracted from the second path 120 and reflected toward DCS detection components. In this example, such DCS detection components can include a refractive element, such as a lens 542, which focuses the light toward a light detector. In certain examples, such as for DCS, the light detector is capable of counting received photons, such as to provide a resulting signal having an intensity that is a function of the photon count, or a resulting signal providing a pulse per photon, or the like. In this example, such a light detector includes individual photomultipliers or an at least 1D (e.g., 1×8) photomultiplier array 544, however, the light detector could include a pigtail of fibers or multiple individual light detectors. In the 1D array example, different locations along the 1D light detector array 544 receive an optical response signal from locations of the target that are different distances away from the incident light beam's location at the target. As described above, this provides information about light that has penetrated to different depths within the target; optical responses obtained at distances that are farther from the incident light beam location are presumed to be responses from light that has penetrated more deeply into the target object 538. In this example, each light detector in the 1D light detector array 544 provides information about its detected light to a correlator 546 circuit. The correlator 546 computes one or more temporal correlation statistics that can be provided to the signal processor circuit 560 to perform DCS. Among other things, such DCS is useful for obtaining blood flow information. An example of obtaining blood flow information from DCS is described in Joseph P. Culver et al., "Diffuse Optical Tomography of Cerebral Blood Flow, Oxygenation, and Metabolism in Rat During Focal Ischemia," *Journal of Cerebral Blood Flow & Metabolism*, 23:911-924, 2003. Detected diffuse light intensity I(r,t) can be detected as a function of distance, r, and time, t. A normalized intensity autocorrelation function of the diffuse light intensity can be computed. This can be used to calculate the diffuse electric field temporal autocorrelation function, which satisfies the correlation diffusion equation. The correlation function decay depends on a constant, k, which can be represented as:

$$k^2 = 3\mu_s'\mu_a + 6\mu_s'^2 k_o^2 \Gamma\tau \quad (1)$$

where τ represents the autocorrelation time delay and $k_o$ represents the photon wavenumber in the medium. The parameter $\Gamma = \alpha D_B$ characterizes blood flow; α represents the probability that a photon is scattered by a moving "cell" and is presumed proportional to cerebral blood volume. The blood flow speed can be parameterized by a Brownian diffusion constant, $D_B$, such as described in Culver et al. and the references cited therein.

As described above, the DCS information can be used to obtain a rendered 3D image that includes information about any changes in the blood flow through the tissue. Moreover, blood flow information can also be used, for example, in determining and displaying a 3D representation of tissue oxygenation, tissue oxygen extraction, or tissue oxygen metabolism. The DCS-derived information is particularly useful in conjunction with the absorption or fluorescence spectroscopic information provided by the LOT concurrent to the DCS information generation.

Moreover, the present DCS configuration, which cleverly uses the x-y scanning from the LOT configuration of FIG. 1, is extremely useful over a DCS system that does not make use of such scanning, but that instead would acquire DCS data either by delivering light to and from tissue using single mode optical fibers, or by using free-space lenses to image a static grid of light sources and light detectors onto the surface of the tissue or other target being imaged. Both would result in low resolution images, with very slow frame rates, since an optical switch would be used to sequentially illuminates the source fibers in their coarse pattern. Moreover, many parallel detection units would be needed to acquire the scattered light, thereby restricting the performance of such a system. By contrast, by using the present x-y scanning, higher resolution, faster, and lower cost DCS information can be obtained-even without using the components of FIG. 5 providing LOT absorption and fluorescence contrast information, if desired.

For example, if only DCS information is desired, components 502, 504, 506, 110, 112, 532, 541, 539, 540, 140, 142, 144, 146, 152, and 148 can be omitted; such an example can still take advantage of the present scanning techniques in conjunction with DCS. If DCS and LOT fluorescence information is desired, components 532, 541, 539 can be added back in, along with at least one of components 502, 504, or 506 and a respective at least one of components 508, 110, or 112. If DCS and LOT absorption information is desired, components 540, 140, 142, 144, 146, 152, and 148 can be added back in, along with at least one of components 502, 504, or 506 and a respective at least one of components 508, 110, or 112. Multi-wavelength LOT absorption information can be obtained using the DCS laser 507 for providing at least one of the multiple wavelengths, if desired. In another example, if LOT absorption and fluorescence information is desired, but DCS information is not desired, the configuration of FIG. 5 can be modified to omit components 540, 542, 544, and 546A-H.

Combining DCS with LOT presents certain technical challenges that the present approach has overcome, such as, for example, how to extract the distinct wavelengths useful for DCS from other wavelengths useful for LOT, and how to perform the different DCS and LOT processing concurrently—particularly where the LOT information can be both spatially-resolved and spectrally-resolved, such as described above with respect to FIG. 1. However, combining DCS with LOT is also useful in an example that does not use a dispersive element 146 to obtain spectrally-resolved and spatially-resolved LOT, but which merely combines spatially-resolved LOT with DCS.

Among other things, the combined LOT/DCS system illustrated in FIG. 5 is capable of concurrently quantifying (1) absorption (and hence oxyhemoglobin and deoxyhemoglobin dynamics in living tissue), (2) fluorescence (such as that from a calcium sensitive or voltage sensitive dye, a targeted molecular probe, or an intrinsic fluorophore such as FAD, NADH, or collagen), and (3) blood flow via DCS.

Although FIG. 5 illustrates separate detection "pathways" for each of fluorescence (e.g., via components 532, 541, and 539), absorption (e.g., via components 140, 142, 144, 146, 152, and 148), and DCS (e.g., via components 540, 542, 544, and 546), this is merely one convenient implementation configuration. In other examples, it is possible to share components and, therefore, reduce the number of components used to implement the system. For example, the 2D light detector array 148 need not Only be used to obtain the LOT absorption response information. Instead, the 2D light detector array 148 can also be used to perform light detection for obtaining the LOT fluorescence information, for obtaining the DCS information, or for obtaining both LOT fluorescence information and DCS information.

For example, to use the 2D light detector array 148 to obtain the DCS information, the correlators 546A-H can be connected to elements in the light detector array 148 that detect the particular wavelength desired for DCS (e.g., 800 nm, in this example). As described above with respect to FIG. 1, the dispersive element 146 is configured to disperse optical response wavelengths along a first dimension of the 2D array, with the perpendicular second dimension of the array representing different lateral optical response locations with respect to incident beam location. Thus, if a particular "row" of the 2D array represents 800 nm optical response at different locations, then the correlators 546 can be individually connected to the light detector elements in that row for obtaining the DCS information. Similarly, if a particular "column" of the 2D array represents 800 nm optical response at different locations, then the correlators 546 can be individually connected to the light detector elements in that column for obtaining the DCS information. Using the 2D light detector array 148 for obtaining LOT absorption and DCS information would allow components 540, 542, and 544 to be omitted.

In another example, the 2D light detector array 148 can be used to obtain the LOT fluorescence response, as well as the LOT absorption response. Since fluorescence response occurs at wavelengths that are different from the wavelength(s) of the incident light, the fluorescence response information can be obtained from the 2D light detector array 148 by ignoring information from those elements that are associated with incident wavelengths. For example, if the incident wavelengths used are 800 nm and 636 nm, which, as the result of the dispersive element 146 correspond to particular "rows" of the 2D light detector array 148, then the fluorescence response information can be obtained from other rows of the 2D light detector array 148. Similarly, if the incident wavelengths used are 800 nm and 636 nm, which, as the result of the dispersive element 146 correspond to particular "columns" of the 2D light detector array 148, then the fluorescence response information can be obtained from other columns of the 2D light detector array 148. In another example, if the incident wavelengths used are 800 nm, 636 nm, 532 nm, and 488 nm, which, as the result of the dispersive element 146 correspond to particular "rows" of the 2D light detector array 148, then the fluorescence response information can be obtained from other rows of the 2D light detector array 148. Similarly, if the incident wavelengths used are 800 nm, 636 nm, 532 nm, and 488 nm, which, as the result of the dispersive element 146 correspond to particular "columns" of the 2D light detector array 148, then the fluorescence response information can be obtained from other columns of the 2D light detector array 148. Using the 2D light detector array for obtaining LOT absorption and LOT fluorescence information would allow components 532, 541, and 539 to be omitted. Using the 2D light detector array for obtaining LOT absorption, LOT fluorescence, and DCS information would allow components 540, 542, 544, 532, 541, and 539 to be omitted.

Although certain examples have been discussed in terms of using a 2D light detector array, multiple 1D light detector arrays could be "stacked" or otherwise used, or a combination of 1D and 2D light detector arrays could be used. This will allow mixing or matching of different detector arrays having different properties, as desired.

Figure 6:
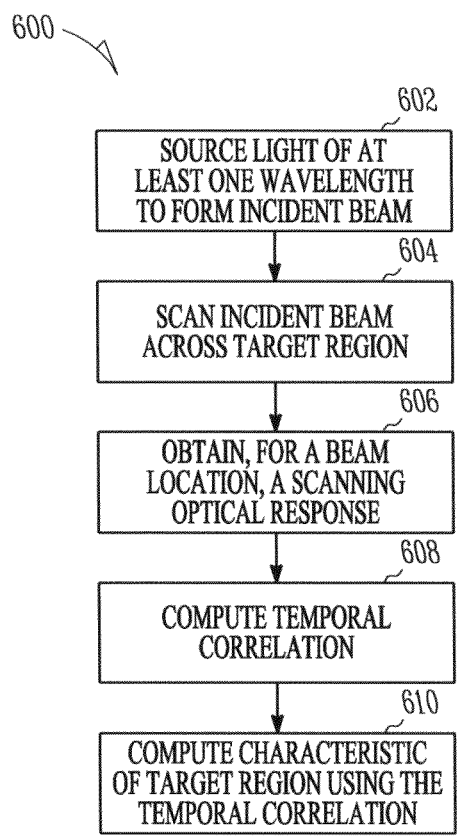
FIG. 6 is a diagram illustrating generally an example of portions of a method that can be performed at least in part by using the system of FIG. 5, if desired, or another system.

FIG. 6 is a diagram illustrating generally an example of portions of a method 600, which can be performed at least in part by using the system of FIG. 5, if desired. At 602, light of at least one wavelength is sourced to form an incident beam. The light generally will include light that has a desired coherence length, such as described above. In certain examples, light of multiple distinct different wavelengths can be provided, such as described above. At 604, the incident beam is scanned across a target region. In certain examples, from this same scanning instance, both DCS and LOT information is obtained, such as described above. At 606, in response to the scanning and for a particular beam location, a scanning optical response signal is obtained. In certain examples, the optical response signal for a particular beam location is obtained at multiple different locations (e.g., different distances) from the incident beam location. In certain examples, the optical response signal includes multiple wavelengths, such as for LOT absorption spectroscopy, for example. In certain examples, the optical response signal includes one or more wavelengths that are different from the one or more incident wavelengths, such as for LOT fluorescence spectroscopy, for example. In certain examples, the optical response signal includes a DCS wavelength that attains at least a particular desired coherence length. At 608, a temporal correlation is computed, such as described above. In certain examples, a temporal correlation is computed for the optical response signal corresponding to each of the multiple different locations (e.g., different distances) from the incident beam location. At 610, a characteristic of the target region is computed using the temporal correlation information. In certain examples, this includes computing one or more of a blood flow characteristic, a tissue oxygenation characteristic, an oxygen metabolism characteristic, or forming or displaying a rendered 3D representation of one or more of such characteristics.

The present inventors have also recognized that using an at least partially flexible optical conduit 130, such as shown in FIG. 1, will in certain situations provide advantages over an example that does not use such an at least partially flexible optical conduit 130, such as the example of FIG. 5 that instead uses a mirror 530, which can be replaced by the optical conduit 130. In certain examples, the at least partially flexible optical conduit 130 can be used to provide a tethered handheld wand for external imaging or spectroscopy. In certain other examples, the at least partially flexible optical conduit can be used to provide a laparoscopic or endoscopic probe such as for carrying out minimally-invasive or other internal diagnostic or prognostic imaging or spectroscopy. For example, this can permit the above-described LOT and DCS techniques to be performed on the oral mucosa, cervix, esophagus, colon, trachea, lung, etc., or performed during surgery, such as by embodying the flexible optical conduit 130 within an at least partially flexible and externally steerable endoscope (such as a colonoscope, for example), which can include flexible and steerable viewing optics.

Figure 7:
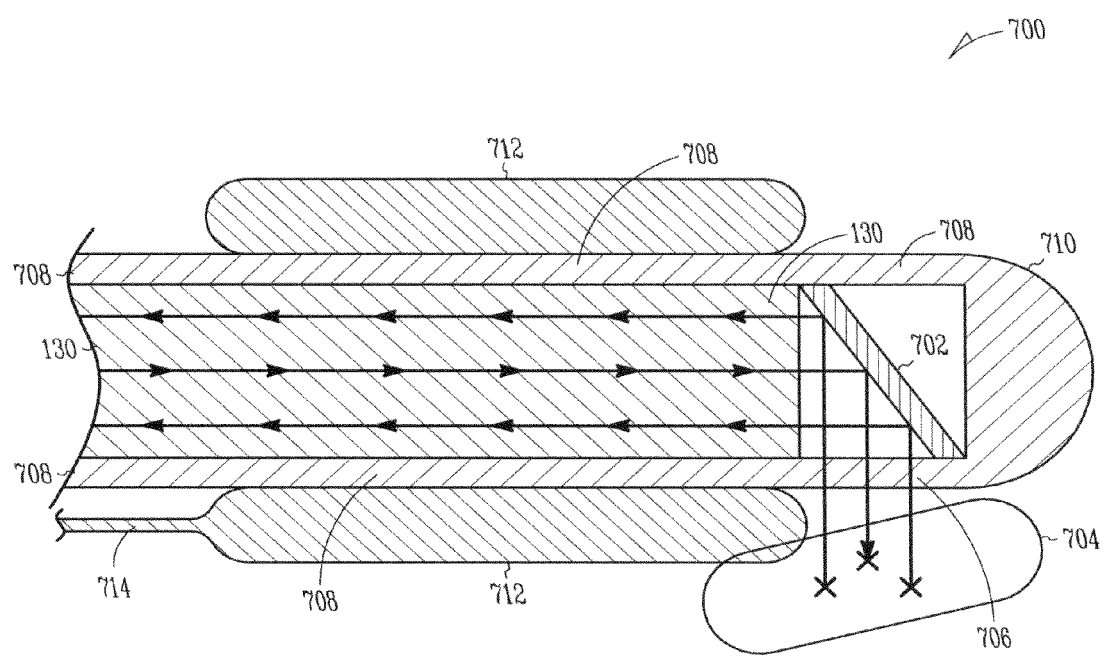
FIG. 7 is a cross-sectional schematic drawing illustrating generally an example of a distal portion of a laparoscope or endoscope that include an optical conduit.

FIG. 7 is a cross-sectional schematic drawing illustrating generally an example of a distal portion 700 of an externally steerable laparoscope or endoscope that includes an optical conduit 130, which in some examples can be at least partially flexible, such as for a laparoscopic or endoscopic LOT, DCS, or other procedure, such as discussed above, to be carried out within a body such as within a body lumen. In certain such applications, it is desirable to obtain a 360 degree or other circumferential image about an interior of the body lumen, such as by using a longitudinal-to-circumferential optical translator guide. In the example of FIG. 7, a rotatable angled mirror 702 or prism can be positioned at the distal portion 700 with respect to the optical conduit 130. In the example shown, a rotatable 45° angled mirror 702 can redirect the incident light beam from along a longitudinal axis of the optical conduit 130 through a transparent (e.g., at the operative wavelengths) window 706 toward a circumferential site 704 on the interior of the body lumen into which the distal portion 700 is inserted. This provides a "side-looking" elongated apparatus. However, the mirror angle can be established or adjusted, such as to additionally or alternatively provide rearward or forward imaging. In this example, the mirror 702 can similarly redirect the optical response from the circumferential site 704 back along the longitudinal axis of the optical conduit 130, such as toward a proximal external location for performing light detection and signal processing, such as described above. The mirror 702 can be rotated about the longitudinal axis of the optical conduit 130, such as to provide full 360° degree imaging or spectroscopy, if desired. In the example of FIG. 7, an outer cylinder 708 with an atraumatic blunt head 710 rotates about the optical conduit 130. A distal portion of the outer cylinder 708 carries the mirror 702 and includes the window 706, such that rotation of the outer cylinder 708 rotates the mirror 702 and the window 706, such as to enable circumferential imaging or spectroscopy. Other techniques may also be suitable for rotating the mirror 702 or otherwise providing circumferential viewing, imaging, or spectroscopy. A dichroic mirror 702 can also be used, for example, to pass at least one different wavelength of light along the longitudinal axis of the optical conduit 130 through the mirror 702 and through an optically transparent head portion 710 (or to another differently-oriented angled mirror). This can provide viewing along the longitudinal axis of the optical conduit 130, which can be helpful for viewing or guiding the distal portion 700 within the body lumen, or even for providing LOT, DCS, or other like capability along the longitudinal axis of the optical conduit 130. In the example of FIG. 7, the variable magnifier 132 can be located at the distal end of the optical conduit 130, near the mirror 702, or at the proximal end of the optical conduit 130.

In certain applications, it can be desirable to fixate the distance between the optical conduit or variable magnifier 132 and the site 704. In certain examples, this can be accomplished by using a transparent window 706 having the desired thickness to maintain the desired separation. In certain examples, this can be accomplished by using a toroidal or other balloon cuff 712 located circumferentially about the distal portion 700. The toroidal balloon cuff 712 can be remotely inflatable, such as via a fluid conduit 714 that extends toward a proximal external end of the endoscopic or laparascopic apparatus. In certain examples, the desired separation can be maintained by a plurality of arms that can be remotely actuated to splay outward or retract inward. Other techniques can also be suitable for maintaining the desired separation.

In certain examples, the side-looking distal end of FIG. 7 uses proximal-end x-y scanning, such provided by the scanner 122 of FIG. 1. However, it may be possible to obtain the desired information without such scanning. For example, movement of the endoscope or laparoscope (e.g., insertion, withdrawal, or rotation) can be used to control the location at which incident light is delivered, or the location where an optical response is obtained. In another example, movement of an element (e.g., mirror 702) within the endoscope or laparoscope (e.g., rotation, telescopic or other extension or retraction) can similarly be used to control the location at which incident light is delivered, or the location where an optical response is obtained.

Figure 8A:
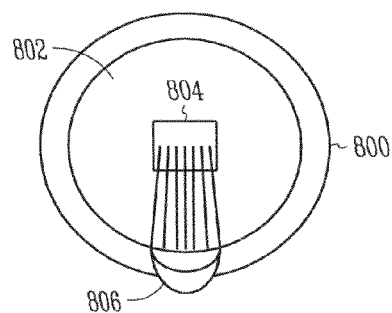
FIG. 8A is a schematic drawing of an example of a cutaway end view of a mirror within an orifice, directing light to and from a region of interest.
Figure 8B:
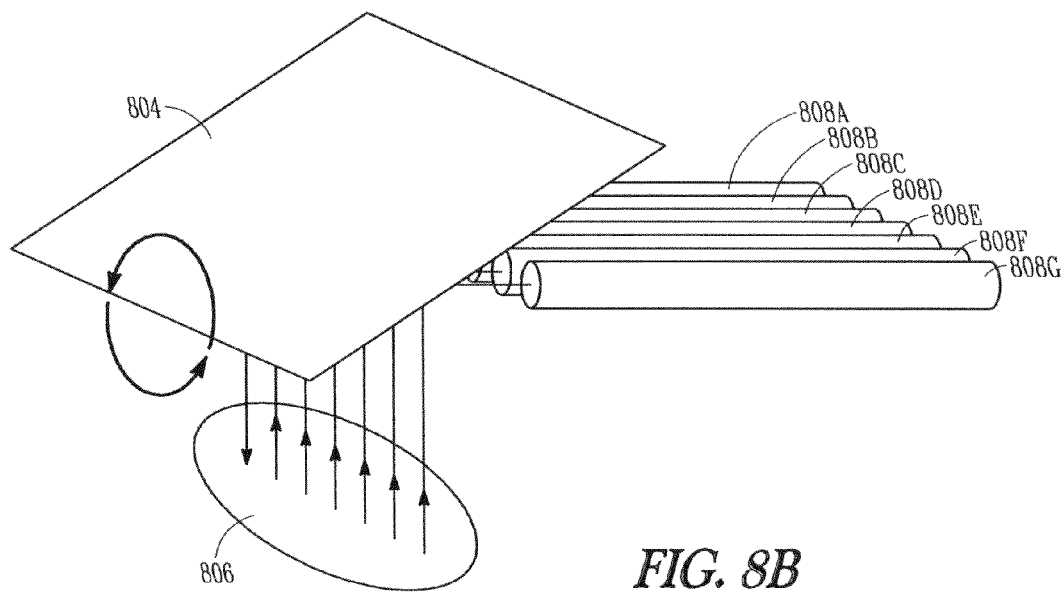
FIG. 8B is a schematic drawing of an example of the mirror together with a linear arrangement of optical fibers.
Figure 8C:
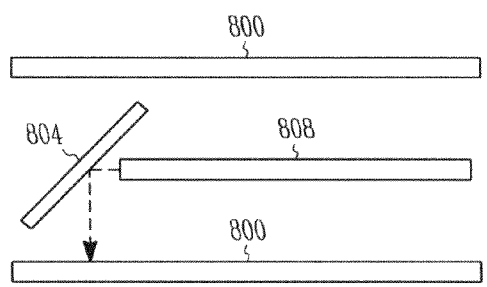
FIG. 8C is a schematic drawing of an example of a cutaway side view of the mirror and fibers within the orifice.

FIGS. 8A, 8B, and 8C provide a schematic example of a side-looking endoscopic or laparoscopic probe for performing optical tomography such as for imaging or spectroscopy. FIG. 8A shows a generally tubular body organ 800, such as a colon, blood vessel, or the like. Within the orifice 802, a longitudinal-to-side optical translator guide, such as a rotatable mirror 804 or prism, can re-direct light from along a longitudinal axis and toward a region of interest 806 on and within the interior wall of the orifice 802. FIG. 8B shows the rotatable mirror 804, with a linear arrangement of optical fibers 808A-G. In this example, the fiber 808A provides incident light to the tissue via the mirror 804. The fibers 808B-G measure the optical response, via the mirror 804, at various lateral distances from the location of the incident light provided by the fiber 808A. In certain examples, one or more of the fibers 808 includes a lens at its distal end, such as a graded refractive index (GRIN) lens, such as for focusing the incident light upon the mirror 804, or for collecting the optical response light from the mirror 804. FIG. 8C shows a side view.

In an example, the mirror 804 rotates together with the linear arrangement of fibers 808—this can be accomplished by rotating the endoscopic apparatus carrying these elements, or by providing rotation of these elements within the endoscopic apparatus carrying these elements. Such rotation permits 360 degree circumferential imaging or spectroscopy within the orifice 802. A back-and-forth rotation can also be used, e.g., a 360 degree rotation in one direction, followed by a 360 degree rotation in the opposite direction. The mirror 804 can also be inserted deeper into the orifice 802 or retracted outward from the orifice 802, together with or independent from the circumferential rotation. This can be accomplished by moving the endoscopic apparatus carrying these elements, or by providing telescopic extension or retraction of these elements within the endoscopic apparatus carrying these elements, or other desired element, such as, for example, a MEMs mirror array to steer the light.

Although the above description has emphasized examples in which light is incident substantially perpendicular to region of interest, the present inventors have also recognized that providing the incident light at a non-orthogonal angle to the region of interest can actually be desirable, and has the potential for providing higher sensitivity and better imaging or spectroscopic resolution. Without being bound by theory, this increased depth sensitivity is believed to be particularly effective at shallow depths, where there is a significant degree of directionality of the light within the tissue. An intersection point between incident light and detected light pathways will provide locations of highest sensitivity for imaging or spectroscopy. In some examples, detection can be performed at an oblique angle and illumination can be performed at a perpendicular angle.

Figure 9:
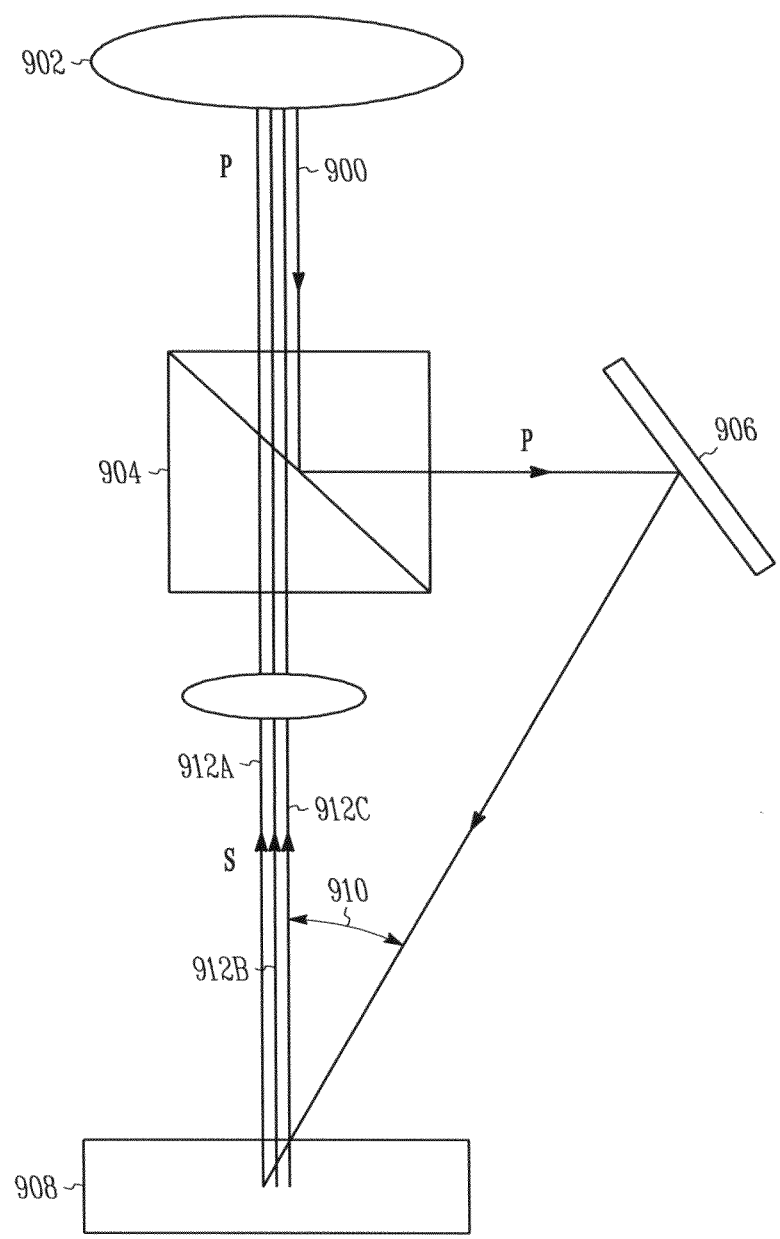
FIG. 9 is a schematic drawing showing an example in which incident light is provided through a lens to a polarizing beam splitter that passes S polarization and reflects P polarization toward a mirror.

FIG. 9 is a schematic drawing showing an example in which incident light 900 is provided through a lens 902 to a polarizing beam splitter 904 that passes S polarization and reflects P polarization toward a mirror 906. The mirror 906 reflects the light with P polarization toward a region of interest 908, where it is incident at a non-perpendicular angle to the region of interest, such as at the angle 910 measured from a line that is perpendicular to the region of interest 908. The scattered incident light will lose its polarization as it is scattered within the tissue of the region of interest 908, and specular reflected light will maintain its P polarization, but such optical response will be rejected upon return to the polarizing beam splitter 904 from the region of interest 908. FIG. 9 also shows optical response detection pathways 912A-C spaced at various lateral distances from the location of the incident light. The optical response returns along the pathways 912A-C through a lens 914 to the polarizing beam splitter 904, which passes light with S polarization on to the lens 902, and to a light detector, such as described above in the other examples. The angled incident beam 906 provides regions of increased sensitivity at the intersections with the optical response return pathways 912A-C, beyond that which could be obtained if the incident light were perpendicular to the target region 908 and laterally spaced from the optical response return pathways 912A-C. The lens 902 can be used to account for the difference in path length of the light diverted by the polarizing beam splitter 904.

The particular angle of incidence 910 can take on any desired value in the range of 0 degrees and 90 degrees. In an example, the angle 910 is between 10 degrees and 80 degrees. In another example, the angle 910 is between 20 degrees and 80 degrees. In another example, the angle 910 is between 10 degrees and 50 degrees. FIGS. 10A-10G are color plots of modeled simulation data illustrating sensitivity functions indicating the most probable paths of the light, with red indicating a larger probability through that particular region, and blue indicating a smaller probability through that particular region. Information detection will be more sensitive in the areas in which there is a larger probability of the light having passed through. In each of FIGS. 10A-10G, the incident light enters the tissue surface, at 1000, at an angle 910 that is 15 degrees from a line perpendicular to the tissue surface. The optical response is measured at 1002 in an orientation that is perpendicular to the tissue surface. The separation distances between the incident location 1000 and response location 1002 are 3.00 mm (FIG. 10A), 2.50 mm (FIG. 10B), 2.00 mm (FIG. 10C), 1.00 mm (FIG. 10D), 0.5 mm (FIG. 10E), 0.2 mm (FIG. 10F), and 0.00 mm (FIG. 10G), respectively. As seen in FIGS. 10A-G, it is possible to tailor the separation distance and the incident angle to select a desired region, to provide increased sensitivity at that desired region, if desired. The angle at which the optical response is detected could also be adjusted, if desired. FIGS. 10A-G also show that, in general, shorter lateral separation distances between incident and response locations are more sensitive to shallower regions, and wider lateral separation distances between incident and response locations are more sensitive to deeper regions.

FIGS. 11A-11G are similar color plots illustrating sensitivity functions, for a 35 degree incident angle 910, and separation distances of 4.00 mm (FIG. 11A), 3.00 mm (FIG. 11B), 2.00 mm (FIG. 11C), 1.50 mm (FIG. 11D), 1.00 mm (FIG. 11E), 0.40 mm (FIG. 11F), and 0.00 mm (FIG. 11G). As seen in FIGS. 11A-G, it is possible to tailor the separation distance and the incident angle to select a desired region to provide increased sensitivity at that desired region, if desired. The angle at which the optical response is detected could also be adjusted, if desired.

In some examples, Monte Carlo simulation can be used to form a reconstruction model that can be used to create the plots of FIGS. 10A-G and 11A-G, respectively. The reconstruction model can also be used to reconstruct an image from the acquired optical response data, if desired. A sensitivity function (such as illustrated in the plots of FIGS. 10A-G and 11A-G) can be defined as:

$$J_{n,m}(r) = \delta M_{n,m}/\delta \mu_a(r). \quad (2)$$

In Equation 2, above, for a given incident light location, n, and a given optical response detection location, m, the sensitivity function $J_{n,m}(r)$ will be a function of the position r within the tissue. $M_{n,m}$ represents a measurement at the tissue surface. $\mu_a(r)$ is the absorption at the position r within the tissue. $\delta M_{n,m}$ represents a change in the measurement $M_{n,m}$. $\delta\mu_a(r)$ represents a change in $\mu_a(r)$. Equation 2 uses the Born approximation, which assumes a linear model relating $M_{n,m}$ and $\mu_a(r)$. The Born approximation assumes that $\delta\mu_a(r)$ is small, so that $J_{n,m}(r)$ can be used to predict $M_{n,m}$. Alternatively, the Rytov approximation can be used, which replaces $\delta\mu_a(r)$ with $\exp(\delta\mu_a(r))$. However, the real relationship relating $M_{n,m}$ and $\mu_a(r)$ is non-linear. Therefore, for larger absorption changes, $\delta\mu_a(r)$, or for other reasons, it may be desirable to use a non-linear reconstruction that updates estimates of $J_{n,m}(r)$ based on the structure of the target object.

From Equation 2, if a modeled sensitivity function $J_{n,m}(r)$ is known, then the absorption $\mu_a(r)$ at various positions within the tissue can be calculated from the measured $\delta M_{n,m}$. Monte Carlo simulation can be used to calculate the modeled sensitivity function $J_{n,m}(r)$. At depths into the tissue that are shorter than the mean scattering length of light in the tissue, directionality of the incident light can be important. Therefore, at such distances into a tissue sample, information about the angles of propagation of the photons can be included in the model. At distances into the tissue that exceed the mean scattering length of the light in tissue, a diffusion approximation to the equation of radiative transport can optionally be used in the model. The radiative transport equation itself can be used in the model, if desired. Moreover, instead of Monte Carlo simulation, empirical measurements or other modeling (e.g., finite element modeling (FEM), finite difference modeling, Maxwell's equations, or the like) can be used to create the reconstruction model.

The reconstruction model can also incorporate any information known about the target object. For example, such known information can be incorporated into the model as one or more constraints upon the model, or as constraints upon 3D or other image reconstruction or spectroscopic information obtained using the model. In an example, if a particular type of target tissue is known, then the model can incorporate information about that particular target tissue type. For example, brain tissue exhibits less light scattering than skin tissue. Therefore, information about the lower scattering of brain tissue can be incorporated into the model. Darker skin exhibits more light absorption than lighter colored skin; this information about a known target can be incorporated into the model. Also, the model can also incorporate spectral information about the particular chromophores expected in that type of target tissue. Similarly, known information about target shape can be used to generate the model. Likewise, information about the particular wavelength of incident light can be incorporated into the model. In certain examples, it is not necessary to actually create a 3D image using the model. Instead, raw data can be processed or presented to a user without actually creating a 3D image. In an example, one can also use a non-linear model that need not require a linearization assumption like Born or Rytov. A look-up table approach could also be used, in an example. In an example, pixel-by-pixel analysis of optical properties and shape functions can be performed without performing a complete image reconstruction.

Although the above description has emphasized an example in which absorption due to light scattering is modeled, a target's fluorescence response can be similarly modeled. Fluorescence results from a photon being absorbed by a fluorophore and a different photon (of longer wavelength) being emitted. Therefore, the amount of fluorescence light emitted will depend on the absorption coefficient of the fluorophore, the quantum yield of the fluorophore (how many incident photons are generally required to trigger the fluorescent emission of a photon), and the concentration of the fluorophore in the target sample of interest. Therefore, fluorescence can be modeled by replacing $\mu_a(r)$ in Equation 2 with a $\mu_{af}(r)$ term denoting fluorescence absorption. Other less simplified models can also be used. For example, because in fluorescence the absorbed photon is of shorter wavelength than the emitted photon, the incoming and emitted photons experience different absorption and scattering, and such differences can be included in the model. The directionality of the incident light is important in modeling scattering events until a fluorophore is encountered, however, since fluorescence emission is generally random in direction, this can also be incorporated into the model. In another example, a combined model of both fluorescence and absorption can also be used, such as to account for interaction between the fluorescence response and the absorption response of a target region of interest. In an example, Raman scattering or other optical contrast can be examined.

Articulating Arm Example

As described above, LOT can allow non-contact depth-resolved optical imaging, such as for example of living tissues to depths even greater than 2 millimeters with on the order of about 100 to 200 micrometer resolution, and with sensitivity to both absorption and fluorescence contrast. In certain examples, LOT can use a beam of light that is scanned over the surface of the tissue, such as by using galvanometer mirrors, such as described above. In response to the scanning beam, light can be detected, such as from areas adjacent to the location of scanning beam upon the target. The further away from the incident beam location that the light has traveled, the deeper that it has traveled into the tissue, and this can thereby be used to provide depth sensitive measurements. Using a model-based reconstruction algorithm, this data can be reconstructed into depth-resolved images of optical contrast, in certain examples, such as described above.

The present inventors have recognized, among other things, that LOT or DCS data can be more conveniently acquired (such as in a clinical setting) using an articulating arm, such as for communicating light to or from the target location, such as the surface of a person's body or any other desired target location. Such an articulating arm can provide three pivots (e.g., correspondingly providing three axes of rotation), which can advantageously be used to allow LOT or DCS techniques to be performed at any desired location on the external surface of the body, for example. Moreover, one or more additional pivots can be further added, such as to further increase the degrees of freedom (e.g., by correspondingly providing further axes of rotation, if desired). In certain examples, the articulating arm setup can be used to allow LOT or DCS techniques to be performed during surgery, such as to help distinguish diseased tissue from normal tissue, for example. In certain examples, the articulating arm setup can be combined with the endoscopic arrangement, such as described above.

The sensitivity of LOT to oxygenation contrast and to both intrinsic (e.g., collagen, NADH, flavoproteins, tryptophan and oxy- and deoxy-hemoglobin, melanin, lipid, water, cytochrome etc.) and exogenous contrast (e.g. voltage, calcium or pH sensitive dyes, molecular probes), as well as the above-described LOT example providing parallelized multispectral detection (sometimes referred to by the present inventors as "SpectraLOT") can produce a highly versatile and relatively inexpensive medical imaging modality with particular suitability to clinical imaging applications, particularly when used with the articulating arm, endoscopic apparatus, or both.

A LOT or DCS system using the articulating arm can be configured in various ways. For example, FIG. 2 shows an illustrative example in which a housing 200 with various optical components is mounted on an articulating arm 202. However, in an example, such as shown in FIG. 2, in which the articulating arm 202 does not provide for optical communication through the articulating arm 202 (e.g., using a separate optical fiber conduit 108), a bulky housing 200 at the distal end of the articulating arm 202 could be needed in order to house the various optical components as shown in FIG. 2. In an example, the articulating arm 202 can include one or more springs, one or more counter-weights, or robotic control, such as for stability or positioning.

Figure 12:
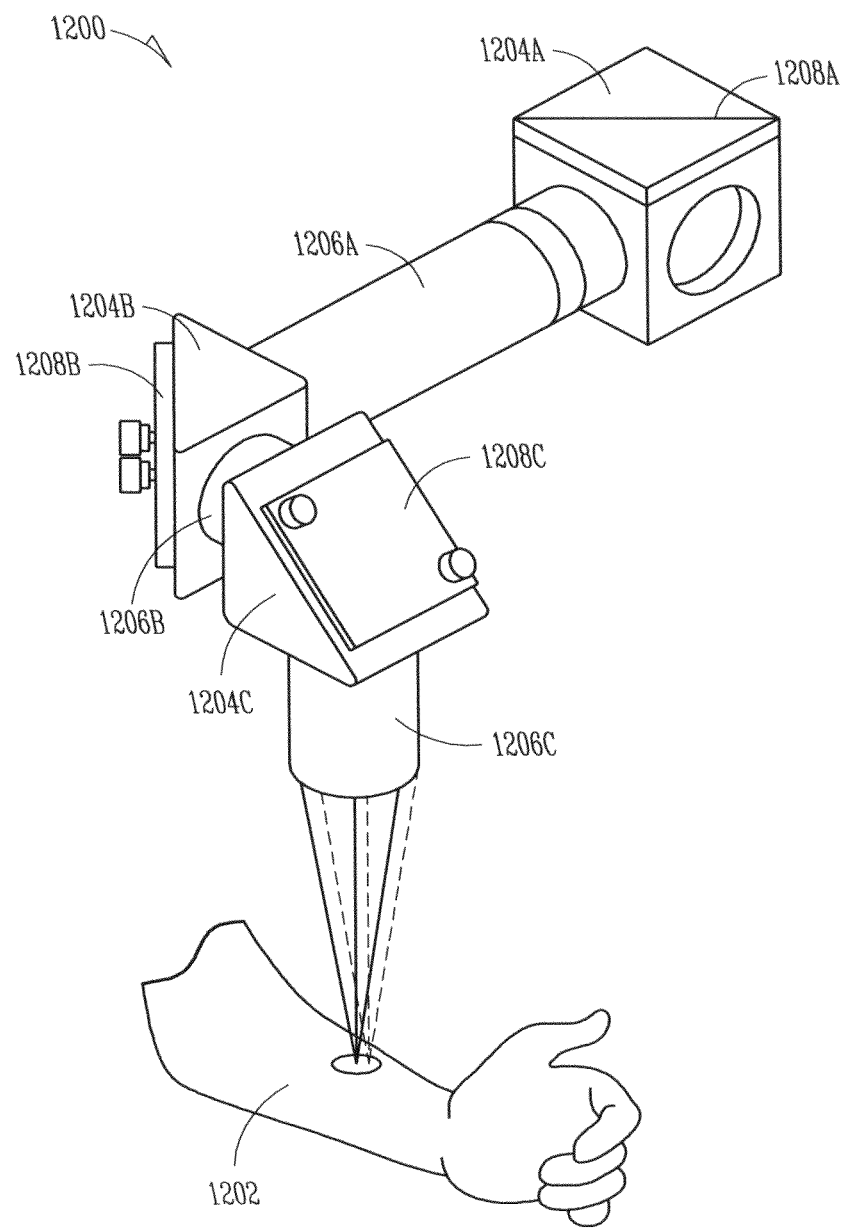
FIG. 12 shows an example of an articulating arm that can provide optical communication along and within the articulating arm itself.

FIG. 12 shows an example of an articulating arm 1200 that can provide optical communication along and within the articulating arm 1200 itself. This allows the optical components to be located at a proximal end of the articulating arm 1200, such that any such bulky optical components can be more conveniently housed away from the subject or object to which LOT or DCS is being applied. In an illustrative example, the housing 200 of FIG. 2 can omit the articulating arm 202. Instead, the housing 200 can be located at proximal end (away from the subject 1202) of the articulating arm 1200. In an example, the articulating arm 1200 can include pivots 1204A-C. Each of the pivots 1204A-C can include or be coupled to a respective cylindrical or other elongated or other segment 1206, along which light can be longitudinally communicated, and an angled (e.g., 45 degree) mirror 1208, to redirect light in a perpendicular direction thereto. The cylindrical segments 1206 can be configured to pivot or rotate about their respective longitudinal axes, such that the combination of the pivoting or rotating segments 1206 and the angled mirrors 1208 provide an adjustable articulating arm 1200 that can communicate light therewithin (e.g., without requiring an optical fiber transmission medium). In an illustrative example, the pivot 1204A can be mounted, in place of the spacer tube 210, to the housing 200. In this way, light for LOT or DCS can be provided via the objective lens 208 into the pivot 1204A, in which it can be perpendicularly redirected by the angled mirror 1208A into the rotatable cylindrical segment 1206A. Then, such light can pass through the segment 1206A into the pivot 1204B, in which it can be perpendicularly redirected by the angled mirror 1208B into the rotatable cylindrical segment 1206B. Such light, in turn, can pass through the segment 1206B into the pivot 1204C, in which it can be perpendicularly be redirected by the angled mirror 1208C into the last cylindrical segment 1206C (which can, but need not, be pivotable or rotatable). Light from the last segment 1206C is directed onto the subject 1200. The return optical signal can traverse a reverse path along the articulating arm 1200.

Figure 13:
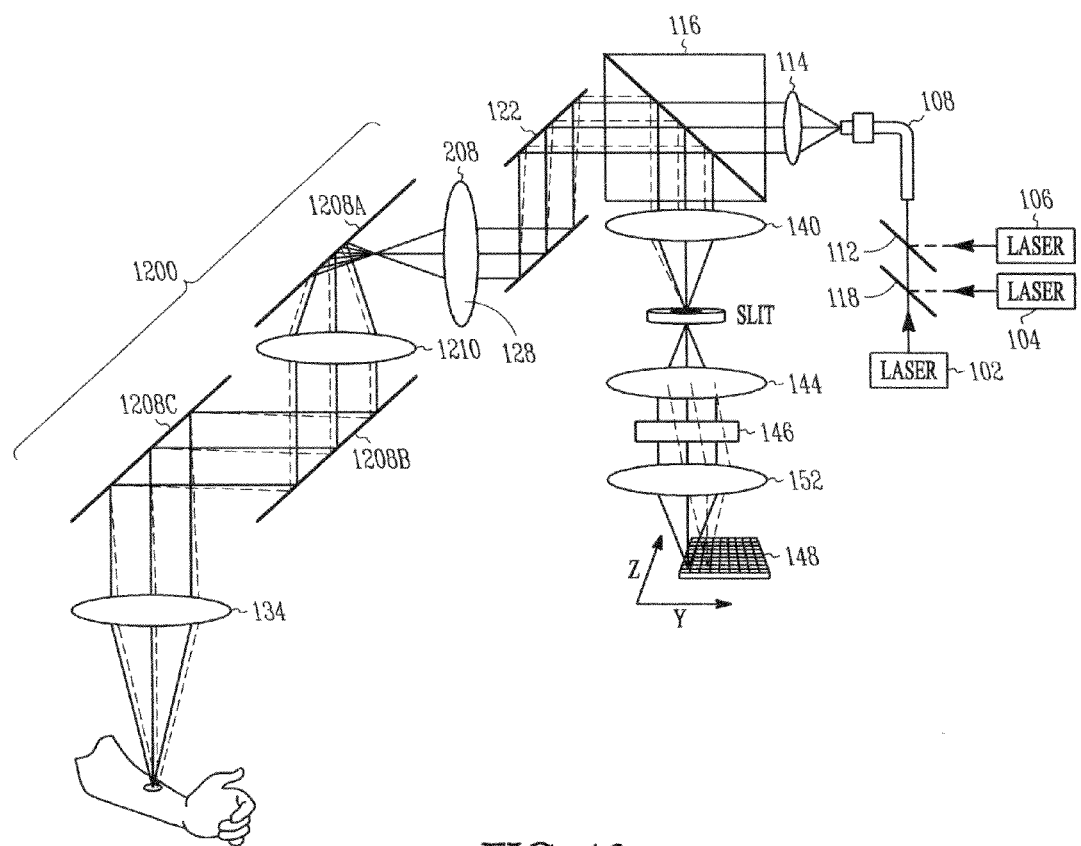
FIG. 13 shows a schematic illustration of components of the articulating arm used in conjunction with LOT components.

FIG. 13 shows a schematic illustration of components of the articulating arm 1200 used in conjunction with LOT components, such as already described in detail above with respect to FIGS. 1, 2, and 12. The segments 1206 can include respective refractive elements, such as refractive lens 1210, as desired. Thus, FIG. 13 shows an illustrative example of the articulating arm 1200 coupling the laser scanning beam to the patient 1200. In the example of FIG. 13, the galvanometer mirrors of the galvanometer 122 provide x and y scanning of the incident beam. Mirrors 1208 located at the pivot joints 1204 of the articulating arm 1200 are positioned so as to perpendicularly redirect the scanning beam, ultimately toward the image plane. The field of view or source-detector separation distances can be adjusted, in certain examples, such as by changing the ratio of the focal lengths of the scan lens 208 and detector lenses 140, 144, and 152.

Figure 14:
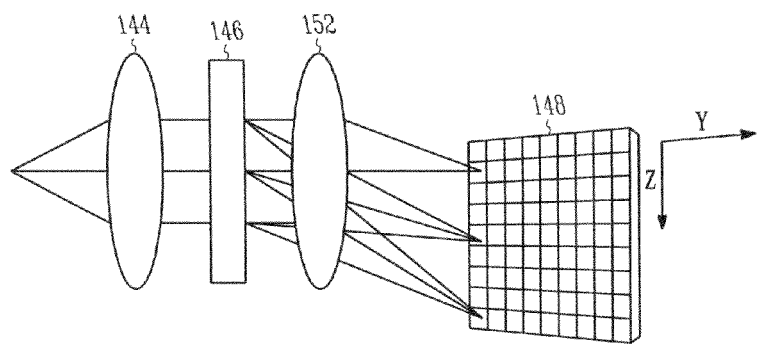
FIG. 14 shows a schematic illustration of how the lenses and the diffraction grating or other wavelength dispersive element can be used to spectrally separate the response signal in the z-direction of the two-dimensional light detector array, with spatial separation of the optical response signal being orthogonal thereto, such as in the y-direction as shown.

FIG. 14 shows a schematic illustration of how the lenses 144 and 152 and the diffraction grating or other wavelength dispersive element 146 can be used to spectrally separate the response signal in the z-direction of the two-dimensional light detector array 148, with spatial separation of the optical response signal being orthogonal thereto, such as in the y-direction as shown in FIG. 14.

Example of Simultaneous Multi-Wavelength LOT Imaging of Skin Cancer

Lentigo maligna (LM) is a lesion in the skin's epidermis. LM mostly occurs in older individuals, such as on sun-damaged skin of the head and neck. The lesions typically appear as a dark brown to tan discoloration on the skin. The lesion boundaries and depth of invasion are difficult to determine. Such information can be very important for proper treatment. Upon extension of the invasion from the epidermis into the dermis, LM is referred to as lentigo maligna melanoma (LMM). The prognosis for LMM is worse than for LM because the dermis contains both vascular and lymphatic networks, thereby providing a metastatic potential. A treatment for LM and LMM is surgical excision of the tumor-containing tissue. Since the lesions typically occur on the face and neck, the surgery has an additional complexity to fully remove the tumor-containing tissue while preserving facial features. At the present time, it is uncertain whether LM will provide good contrast, because (without being bound by theory) the edges are believed not usually high in melanin. However, it is believed that other dermatology applications can also benefit from the present systems and methods.

Figure 15:
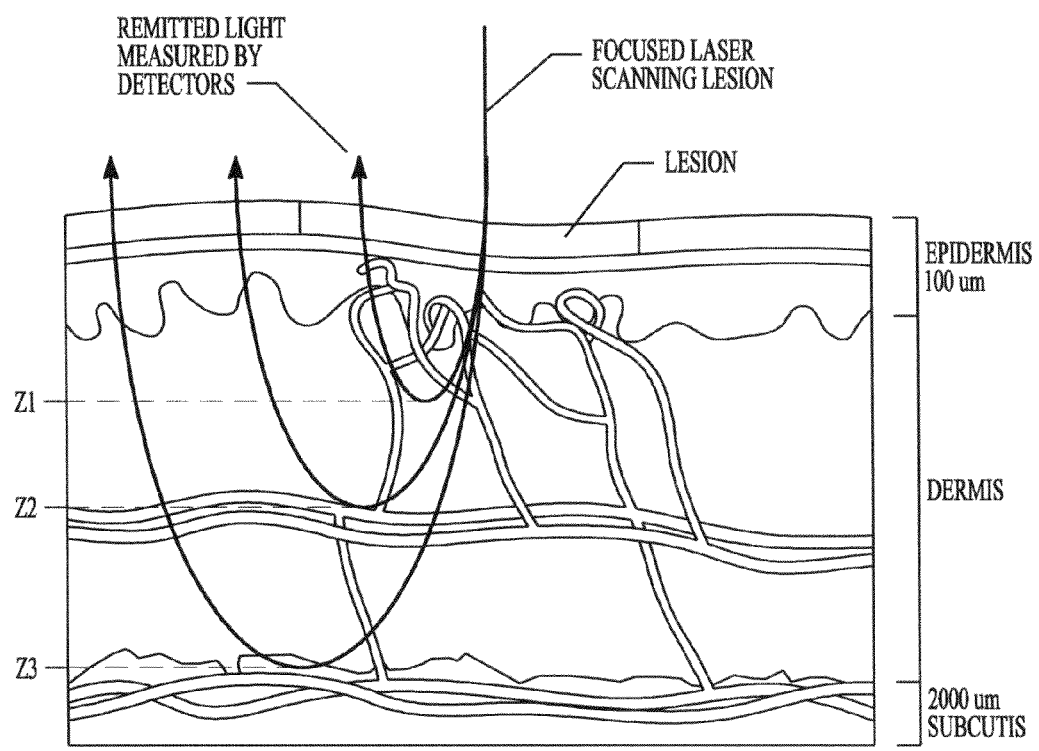
FIG. 15 shows an example of a cross sectional schematic view of skin imaging.

FIG. 15 shows an example of a cross sectional schematic view of skin imaging, such as with respect to skin that, in this example, includes an epidermis layer extending from the surface to a depth of about 100 μm below the surface, a cutis layer beginning at about 2000 μm below the surface, and a dermis layer located between the epidermis and the cutis layers. In this example, a focused laser beam can be scanned over the skin surface, such as at the location of a lesion. Light remitted at locations further from that of the incident laser beam provides information about deeper subsurface (e.g., at z1, z2, z3) optical properties of the tissue. LOT can be used for imaging skin lesions. As described above, LOT can provide a non-contact imaging system capable of depth-resolved imaging, such as, for example, to depths of up to about 2 mm with up to about 100-200 μm resolution at up to about 100 frames per second. LOT can scan a focused laser beam over tissue and measure the scattered light emerging at successive lateral distances of up to 2.5 mm away from the scanning location, such as shown in the example of FIG. 15. The response light measured at further distances from the focused incident scanning spot can reveal respectively deeper subsurface absorption and fluorescence properties of the tissue. For example, LOT can be used to measure the depth-resolved absorption properties of melanin, oxyhemoglobin, or deoxyhemoglobin.

Melanocytes, the pigment (melanin) producing cells in the epidermis, are the cells that become cancerous in malignant melanomas. At present, the discoloration associated with an increased concentration of melanin is generally the surgeon's primary way of determining surgical margins of LM. However, in some cases, the true margins of LM extend beyond the area of pigmentation visible from the surface. This can lead to re-excisions or recurrence of the disease.

Dermal vascularity is expected to significantly increase beneath in situ LMM, such as compared with normal skin or when LM is present without dermal invasion, in which cases the vascularity is believed less likely to significantly differ from surrounding skin. Therefore, LOT's ability to measure the amount, and oxygenation state of blood beneath a lesion can be useful for surgical staging or further treatment planning.

While LOT can be used for studying hemodynamics, such as in the exposed rodent brain, it can also be configured for clinical use. By way of example, but not by way of limitation, it can be used to acquire simultaneous three-wavelength measurements of skin. Among the benefits of making multi-wavelength spectroscopic measurements simultaneously are that doing so allows very rapid acquisition, and precise spectroscopy of skin chromophores. If images of three wavelengths were acquired sequentially, there would be significant risk of the patient moving, which would prevent accurate pixel-by-pixel analysis of the resulting data. LOT can provide the surgeon with a tool to help pre-surgical planning. LOT can be used to measure the depth of invasion and to provide measurements that allow the surgeon to better delineate the tumor boundaries. By simultaneously scanning and measuring 3 wavelengths of light, LOT could provide accurate measurements of subsurface melanin, oxy-hemoglobin (HbO) concentration, or deoxy-hemoglobin (HbR) concentration. Such measurements could help enable more precise excisions around the tumor-containing tissue, thereby minimizing the amount of tissue removed, such as near important facial features.

Figure 16:
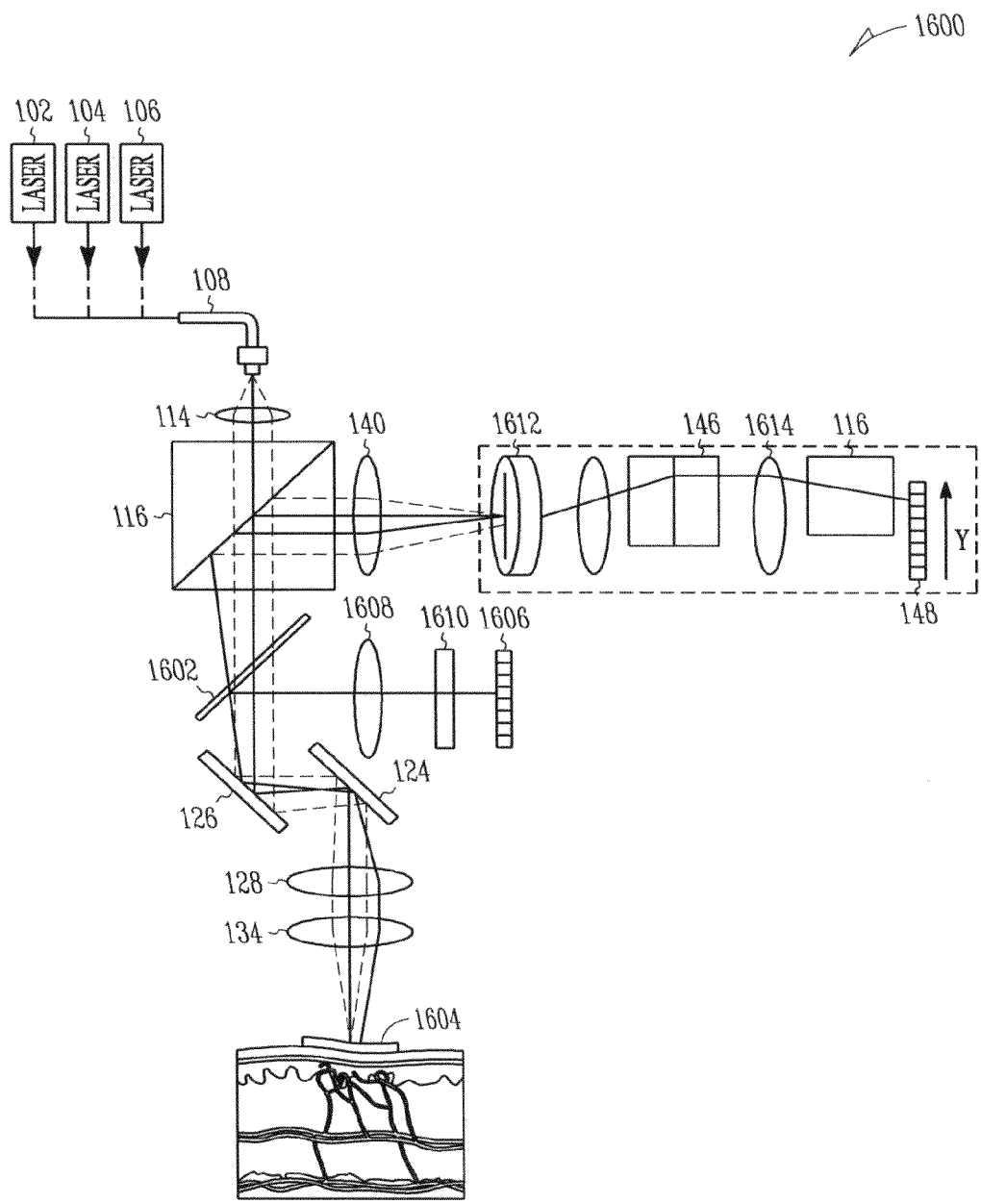
FIG. 16 shows a schematic drawing of an example of a LOT system, such as for skin imaging.

FIG. 16 shows a schematic drawing of an example of a LOT system 1600 that can include multiple (three, in this example) lasers, such as the laser 106 (e.g., 85-BCD-030-115, Melles Griot) providing light of wavelength of 488 nm, the laser 104 (e.g., 85-GCA-020, Melles Griot) providing light of wavelength of 532 nm, and the laser 102 (e.g., 56RCS004/HS, Melles Griot) providing a light of a wavelength of 638 nm. Light from the lasers 102, 104, and 106 can be collinearly aligned into a single polarization maintaining single mode fiber 108. The resulting multi-wavelength beam can then be emitted from the other end of the fiber 108, collimated (e.g., using the lens 114) and passed through a polarizing beam splitter 116 cube and a 3-line dichroic filter 1602 before being reflected by an x-scanning mirror 124 and a y-scanning mirror 126 of a galvanometer 122. The galvanometer mirrors 124, 126 can scan the beam through an f=30 mm scan lens 128 before passing through a 1× objective or other lens 134 and onto the tissue 1604.

While the multi-wavelength incident beam is scanned over the region of interest, scattered light emerging from the tissue travels back through the objective lens 134, through the scan lens 128 and onto the galvanometer mirrors 124, 126. The mirrors 124, 126 de-scan the remitted light, directing it back towards the dichroic 1602 and the polarizing beam splitter 116 cube. Fluorescent response light (at wavelengths different from that of the incident light) can be redirected by the dichroic 1602 to a fluorescence detector, such as the 1×16 photomultiplier tube (PMT) array 1606, via the lens 1608 and filter 1610.

Of the remaining response light, which continues through the dichroic 1602 to the polarizing beam splitter 116, specular reflections will have maintained their P polarization, and will not be reflected by the polarizing beam splitter 116. However, the scattered response light should be randomly polarized. Therefore, approximately half of the scattered response light will be reflected by the polarizing beam splitter 116 toward the "absorption" detector portion of the system 1600. This light then passes through a magnification lens 140 on its way to a slit 1612. The light passing through the slit 1612 emerges as a line of multi-wavelength light. The center of this line of multi-wavelength light corresponds to on-axis light, while light further from the center of this line corresponds to the light emerging from the tissue 1604 at successive distances from the location of the incident light beam spot sourced onto the tissue 1604. This line of light emerging from the slit 1612 can pass through a dispersion element 146, such as a prism (e.g., PS853, Thorlabs), which can separate the light into three lines of distinct wavelengths. The three distinct lines of light can be redirected by a mirror or lens 1614 and passed through a second polarizing beam splitter 116 cube, such as to remove any residual P-polarized light, before being projected onto a detector 148, such as an 8×8 two-dimensional PMT light detector array (e.g., H7546B, Hamamatsu). The combined use of a prism 146 (or other dispersive element) and a two-dimensional light detector array 148 permits simultaneous detection of light with multiple wavelengths and different depth-sensitivities, such as described above. The system magnification can be configured such that the distance between channels on the PMT 2-D array 148, when projected onto the object plane at the tissue 1604, can be reduced to the desired source-detector separation distance (e.g., 1.2 mm distance, at the array 148, can correspond to 200 µm distance at the tissue 1604). A 24-channel transimpedance amplifier can be coupled to the outputs of the channels of the PMT array 148, such as to convert the current output of each PMT channel into a voltage signal. In an illustrative example, the system 1600 can use four 8-channel simultaneous sampling data acquisition boards (e.g., NI PCI-6133, National Instruments, 3 MHz sample rate per channel) to sample the signal from each of the 24 channels (3 lines) on the 2D array PMT, and 7 channels on the linear fluorescence PMT. Acquisition speed can be limited by the galvanometric scanners (average maximum speed, about 4500 lines per second). Therefore, 100×100 source-position data can be acquired at 45 frames per second (fps), and 40×40 source-position data can be acquired at over 100 fps. The $8^{th}$ channel on the fluorescence data acquisition card can be used to monitor the position of the x-galvanometer mirror.

Synchronization and control of the LOT system 1600 can be achieved using a Matlab Graphical User Interface, in an example. The control software allows the user to change one or more parameters such as the field of view, pixels per frame, frame rate, or number of lasers used. Following a scan, the measured data can be processed in hardware or software, such as by a signal processor or other circuit 160, into an image (or any of the plurality (e.g., 32) of simultaneously acquired images) and displayed on a screen, such as a display provided by a user interface 162, such as described above with respect to FIG. 1. Analysis for converting the images into 3D reconstructions can be performed offline, such as described above and in: (1) Hillman, E. M., et al., *Laminar optical tomography: demonstration of millimeter-scale depth-resolved imaging in turbid media*. Opt Lett, 2004. 29(14): p. 1650-2; (2) Hillman, E. M., et al., *Depth-resolved optical imaging and microscopy of vascular compartment dynamics during somatosensory stimulation*. Neuroimage, 2007. 35(1): p. 89-104; and (3) Hillman E. M. et al. "*Depth-resolved optical imaging of transmural electrical propagation in perfused heart*", Optics Express. 15 (26), 17827-17841 (2007), each of which is incorporated herein by reference in its entirety, including its description of converting the images into 3D reconstructions.

Figure 17:
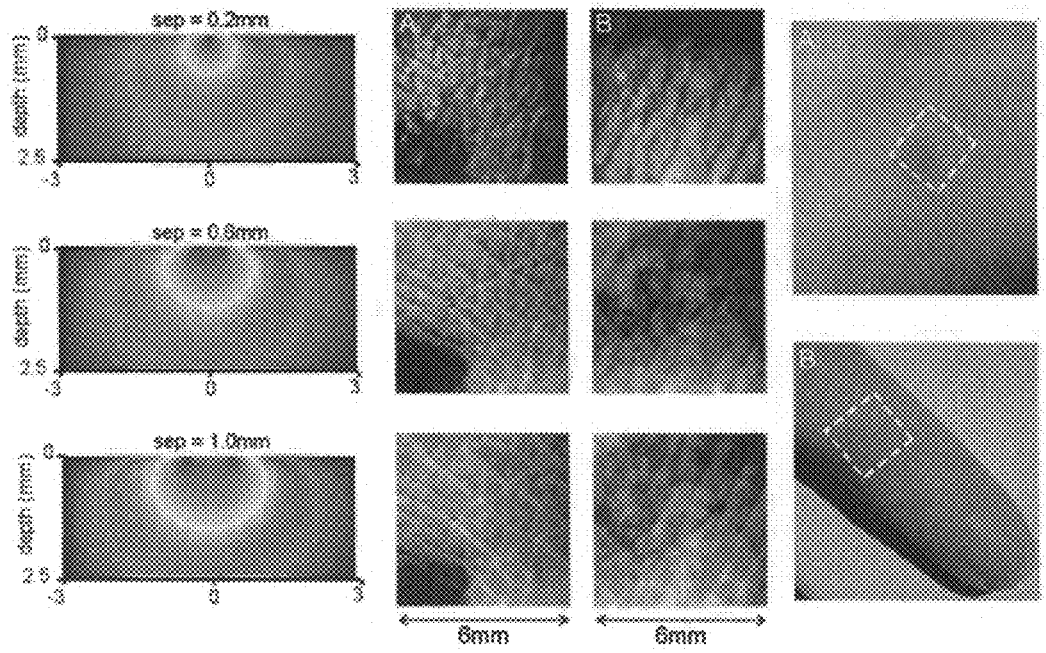
FIG. 17 shows information relating to skin imaging. The left-most images show Monte-Carlo simulations of the likely paths of light for three source-detector separations: (1) 0.2 mm, top left image; (2) 0.6 mm, middle left image; and (3) 1.0 mm, bottom left image. The middle images show raw imaging data acquired on a benign mole (A) and amelanotic erythema (B), for the same three source-detector separations. The right-most images are photographs of the mole (A) and amelanotic erythema (B).

FIG. 17 shows an example of early data acquired using a LOT system to perform multi-spectral acquisition, although this data is from experiments in which the multi-spectral acquisition was performed serially, rather than in parallel as described above. In this example, two benign lesions, a mole and amelanotic erythema, were imaged using LOT. The resulting measurements were merged into red-green-blue images. These images depict LOT data in its "raw" form, representing a series of boundary measurements for 100× 100 source positions for three different source-detector separations. This data can be substantially downsampled before 3D LOT "reconstruction" such as to discern invasion depth or to quantitatively extract HbO, HbR, or melanin concentrations. However, these raw images of FIG. 17 demonstrate the significant value of this non-contact, high-speed multi-spectral imaging tool.

In FIG. 17, the left-most images show Monte-Carlo simulations of the likely paths of light for three source-detector separations: (1) 0.2 mm, top left image; (2) 0.6 mm, middle left image; and (3) 1.0 mm, bottom left image. The middle images in FIG. 17 show 6 mm×6 mm raw imaging data acquired on a benign mole (A) and amelanotic erythema (B), for the same three source-detector separations: (1) 0.2 mm, top images; (2) 0.6 mm, middle images; and (3) 1.0 mm, bottom images. The right-most images are photographs of the mole (A) and amelanotic erythema (B). The middle images shown in FIG. 17 are red-green-blue merge bitmaps of the data from red, green and blue lasers. In these images, the brown melanin and red hemoglobin can clearly be distinguished. The close source-detector separations reveal the rough surface of the skin. The wide separations more clearly reveal the sub-surface absorbing structure. The blueish hue to the superficial images corresponds to wavelength-dependent back-scatter.

In FIG. 17, the close source-detector separations can reveal features near the surface of the skin. The wider source-detector separations can enhance visualization of sub-surface structures, even without subsequent 3D analysis. In FIG. 17, the mole image data (A) shows brown melanin in each source-detector separation image In FIG. 17, the amelanotic erythema image data (B) lack melanin, but show red hemoglobin contrast. In FIG. 17, the amelanotic erythema data (B) also indicate that the hemoglobin was not present at the surface of the skin, which is consistent with the vasculature of the skin. This data demonstrates that multi-wavelength LOT can provide highly valuable clinical information. Clinical trials can be undertaken to acquire LOT measurements on patients with LM or LMM before surgical excision. This can quantitatively compare our "raw" and reconstructed in-vivo data to the histology of the same excised tissue to further help establish the diagnostic or prognostic potential of LOT for this application.

Figure 18:
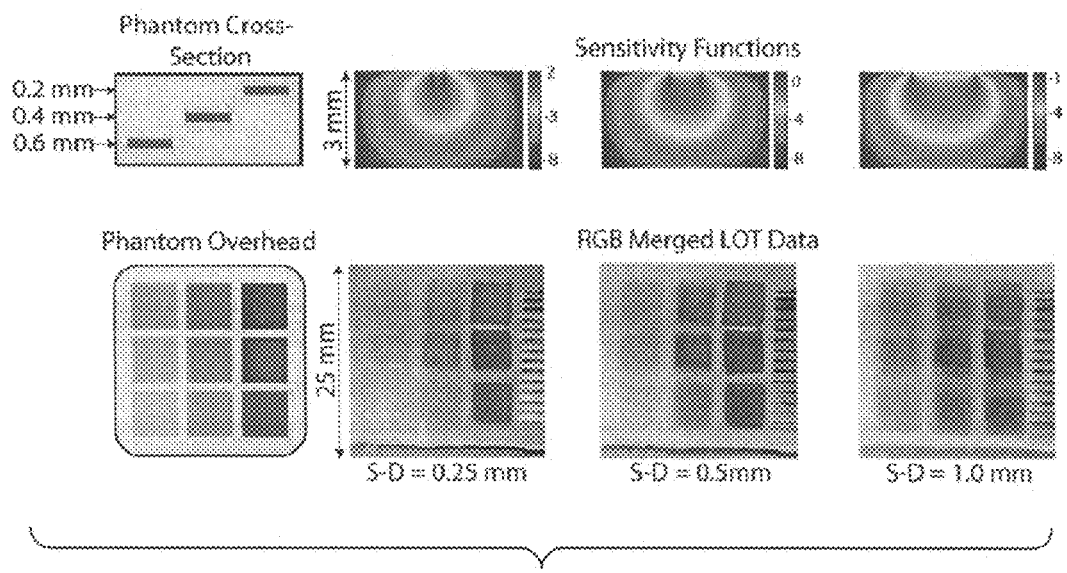
FIG. 18 shows an example of simultaneously-acquired multi-spectral LOT LOT data obtained using a test phantom as the object being imaged.

FIG. 18 shows an example of simultaneously-acquired multi-spectral LOT LOT data obtained using a test phantom as the object being imaged. FIG. 18 shows examples of cross-sectional and overhead views of the test phantom. A mixture of interlipid, agarose, and bovine hemoglobin was prepared and disposed at various depths (e.g., 0.2 mm, 0.4 mm, and 0.6 mm) of the phantom. The modeled sensitivity functions in FIG. 18 correspond to different source-detector separations distances (e.g., 0.25 mm, 0.5 mm, and 1.0 mm), and can be used for image reconstruction, such as described above, to produce the corresponding simultaneously-acquired multi-spectral RGB Merged LOT Data of FIG. 18. The simultaneously-acquired multi-spectral RGB LOT Data of FIG. 18 demonstrates that a wider source-detector separation can exhibit a better contrast to a deeper object, and the narrower source-detector separation can exhibit a better contrast to shallower object.

Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine-implemented or computer-implemented at least in part. Some examples can include a tangible computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method, comprising:
   sourcing light at different wavelengths concurrently to form an incident beam;
   communicating the light along an articulated arm that does not use a fiber optic conduit;
   scanning a location of the incident beam including the different wavelengths across a target region at a selectable incident angle to the target region;
   obtaining an optical response concurrently at different locations at different distances in a first direction from the beam location upon the target region, the different distances corresponding to respective different depths penetrated by the incident beam at the selectable incident angle within the target region;
   spectrally separating different wavelengths of the obtained optical response; and
   detecting the spectrally separated wavelengths of the obtained optical response from the different locations concurrently to provide information about the target region.

2. The method of claim 1, in which detecting the spectrally separated wavelengths of the obtained optical response includes detecting a first and second wavelengths of fluorophore emission, wherein the first wavelength of fluorophore emission is different and spectrally separated from the second wavelength of fluorophore emission.

3. The method of claim 2, in which detecting the spectrally separated wavelengths of the obtained optical response includes detecting the first wavelength of fluorophore emission from a first type of fluorophore and detecting the second wavelength of fluorophore emission from a second type of fluorophore that is different from the first type of fluorophore.

4. The method of claim 3, in which the spectrally separating different wavelengths of the obtained optical response includes spectrally separating along a linear second direction that is orthogonal to the first direction at a light detector.

5. The method of claim 4, further comprising:
storing a two-dimensional array of the spectrally separated obtained optical response information from the light detector for different beam locations of the target region; and
using the stored two-dimensional array of the spectrally separated obtained optical response information from the light detector for different beam locations of the target region to construct at least one of:
a three dimensional rendered image of the target region;
an image representing chemical composition of the target region; and
a plurality of images representing information about different depths of the target region.

6. The method of claim 1, in which the spectrally separating different wavelengths comprises refracting different wavelengths by different amounts.

7. The method of claim 1, in which the spectrally separating different wavelengths comprises diffracting the different wavelengths by different amounts.

8. The method of claim 1, in which the spectrally separating different wavelengths includes filtering a first wavelength from a second wavelength.

9. The method of claim 1, further comprising:
computing, for the multiple different lateral locations, a measured value of a temporal correlation of the scanning optical response; and
computing a first characteristic of the target region using the measured value of a temporal correlation.

10. The method of claim 9, further comprising:
obtaining, in response to the same scanning, a fluorescence component of the scanning optical response signal; and
using the fluorescence component of the scanning optical response signal to compute a second characteristic of the target region.

11. The method of claim 10, further comprising:
obtaining, in response to the same scanning, an absorption component of the scanning optical response signal; and
using the absorption component of the scanning optical response signal to compute a third characteristic of the target region.

12. The method of claim 10, further comprising:
obtaining, in response to the same scanning, an absorption component of the scanning optical response signal, the absorption component comprising at least two different wavelengths of light; and
using the absorption component of the scanning optical response signal to compute a third characteristic of the target region.

13. The method of claim 1, further comprising using an optical conduit to communicate light to and from the target region.

14. The method of claim 13, wherein the scanning an incident beam location and obtaining an optical response are carried out for a target location that is internal to a human or animal.

15. The method of claim 1, wherein the scanning an incident beam location and obtaining an optical response are carried out for a target location that is orthogonal to a longitudinal axis of the optical conduit.

16. The method of claim 1, further comprising:
scanning the location of the incident beam across a target region comprising skin; and
using the information about the target region to discriminate between first and second skin conditions.

17. The method of claim 1, further comprising using an oblique angle from the target region for at least one of the scanning or the obtaining the optical response.

18. The method of claim 1, further comprising:
computing, for the multiple different lateral locations, a measured value of a temporal correlation of the scanning optical response; and
computing a blood flow characteristic of the target region using the measured value of a temporal correlation.

19. The method of claim 1, further comprising using an oblique angle from the target region for the scanning, and obtaining the optical response from an intersection point between the oblique incident light and detected optical response light pathways.

20. An apparatus comprising:
at least one light source including at least one of a laser, a light-emitting diode, or a lamp, the light source providing at least one wavelength of light, the at least one light source contained in a housing;
a scanner, configured to receive the light from the light source, and configured to scan a beam of the light across a target region at a selectable incident angle to the target region;
a light detector, configured to receive from the target region a scanning response signal at a plurality of distances from a beam location upon the target region, the plurality of distances from the beam location upon the target region corresponding to respective different depths penetrated by the beam at the selectable incident angle within the target region to generate respective different wavelengths of the response signal at the plurality of distances from the beam location upon the target region;
a dispersive element including at least one of a prism, diffraction grating, or one or more dichroic filters, the dispersive element configured with respect to the light detector to direct a first wavelength of the scanning response signal to a different location of the light detector than a second wavelength of the scanning response signal, wherein the second wavelength is different from the first wavelength; and
an articulating arm, configured to communicate light along the articulating arm, between the housing and the target region, without requiring a fiber optic conduit.

21. The apparatus of claim 20, comprising a signal processor circuit, coupled to the light detector, the signal processor circuit further configured to concurrently process the scanning response signal of the first wavelength and the scanning response signal of the second wavelength; and
wherein the lateral distances define a linear first direction, and wherein the dispersive element is configured to spatially separate wavelengths of the scanning response signal in a linear second direction that is orthogonal to the first direction;

wherein the light detector includes a two-dimensional array of light detector elements, and is configured to detect different wavelengths of the scanning response signal along a first dimension of the two-dimensional array, and to detect along a second dimension of the two-dimensional array optical responses from the different lateral distances from the beam location, and wherein the first and second dimensions of the two-dimensional array are orthogonal to each other, and comprising an imaging data memory including a two-dimensional array of memory locations for corresponding scanning locations of the target region, each two-dimensional array of memory locations storing data from the two-dimensional array of light detectors for a particular scanning location of the target region.

22. The apparatus of claim 20, wherein the light source comprises:

a first laser, providing laser light at the first wavelength; and a second laser, providing laser light at the second wavelength that is different from the first wavelength, and wherein the first wavelength of the scanning response signal is in response to the first wavelength of laser light provided by the first laser, and wherein the second wavelength of the scanning response signal is in response to the second wavelength of laser light provided by the second laser;

wherein the first wavelength of the scanning response signal is in response to a first emission wavelength of a first fluorophore, and wherein the second wavelength of the scanning response signal is in response to a second emission wavelength of a second fluorophore of the same type as the first fluorophore or of a different type than the first fluorophore.

23. The apparatus of claim 20, wherein the apparatus further comprises:

a beam splitter configured to communicate light with the scanner and the dispersive element.

24. An apparatus, comprising:

at least one light source, contained in a housing, providing at least one wavelength of light;

a scanner, configured to receive the light from the light source, and configured to scan a beam of the light across a target region at a selectable incident angle to the target region;

a light detector, configured to receive from the target region a scanning response signal at a plurality of distances from a beam location upon the target region, the plurality of distances corresponding to respective different depths penetrated by the light at the selectable incident angle within the target region;

a dispersive element including at least one of a prism, diffraction grating, or one or more dichroic filters, the dispersive element configured with respect to the light detector to direct a first wavelength of the scanning response signal to a different location of the light detector than a second wavelength of the scanning response signal, wherein the second wavelength is different from the first wavelength;

a signal processor circuit, coupled to the light detector, the signal processor circuit configured to concurrently process the scanning response signal of the first wavelength and the scanning response signal of the second wavelength; and wherein the lateral distances define a linear first direction, and wherein the dispersive element is configured to spatially separate wavelengths of the scanning response signal in a linear second direction that is orthogonal to the first direction;

wherein the light detector includes a two-dimensional array of light detector elements, and is configured to detect different wavelengths of the scanning response signal along a first dimension of the two-dimensional array, and to detect along a second dimension of the two-dimensional array optical responses from the different lateral distances from the beam location, and wherein the first and second dimensions of the two-dimensional array are orthogonal to each other, and comprising an imaging data memory including a two-dimensional array of memory locations for corresponding scanning locations of the target region, each two-dimensional array of memory locations storing data from the two-dimensional array of light detectors for a particular scanning location of the target region;

wherein the light source comprises:

a first laser, providing laser light at the first wavelength; and a second laser, providing laser light at the second wavelength that is different from the first wavelength, and wherein the first wavelength of the scanning response signal is in response to the first wavelength of laser light provided by the first laser, and wherein the second wavelength of the scanning response signal is in response to the second wavelength of laser light provided by the second laser;

wherein the first wavelength of the scanning response signal is in response to a first emission wavelength of a first fluorophore, and wherein the second wavelength of the scanning response signal is in response to a second emission wavelength of a second fluorophore of the same type as the first fluorophore or of a different type than the first fluorophore; and wherein the apparatus further comprises:

a beam splitter configured to communicate light with the scanner and the dispersive element; and an articulating arm, configured to communicate light along the articulating arm, between the housing and the target region, without requiring a fiber optic conduit.

* * * * *

UNITED STATES PATENT AND TRADEMARK OFFICE
CERTIFICATE OF CORRECTION

PATENT NO. : 9,655,523 B2  
APPLICATION NO. : 12/655325  
DATED : May 23, 2017  
INVENTOR(S) : Elizabeth Marjorie Clare Hillman et al.

Page 1 of 1

It is certified that error appears in the above-identified patent and that said Letters Patent is hereby corrected as shown below:

In the Specification

The paragraph at Column 1, Lines 37-44 should read as follows:
--STATEMENT REGARDING FEDERALLY SPONSORED RESEARCH
This invention was made with government support under Grant NS053684 awarded by the National Institutes of Health. The Government has certain rights in this invention.--

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*